(12) United States Patent
Robinson et al.

(10) Patent No.: US 12,122,805 B2
(45) Date of Patent: Oct. 22, 2024

(54) DENDRITIC DETERGENTS FOR THE ANALYSIS OF PROTEINS BY MASS SPECTROMETRY

(71) Applicants: OXFORD UNIVERSITY INNOVATION LIMITED, Oxford (GB); FREIE UNIVERSITÄT BERLIN, Berlin (DE)

(72) Inventors: Carol V. Robinson, Oxford (GB); Idlir Liko, Oxford (GB); Hsin-Yung Yen, Oxford (GB); Kevin Pagel, Berlin (DE); Rainer Haag, Berlin (DE); Svenja Christina Ehrmann, Berlin (DE); Leonhard Hagen Urner, Berlin (DE)

(73) Assignees: OXFORD UNIVERSITY INNOVATION LIMITED, Oxford (GB); FREIE UNIVERSITÄT BERLIN, Berlin (DE)

( * ) Notice: Subject to any disclaimer, the term of this patent is extended or adjusted under 35 U.S.C. 154(b) by 854 days.

(21) Appl. No.: 17/272,614

(22) PCT Filed: Sep. 4, 2019

(86) PCT No.: PCT/GB2019/052462
§ 371 (c)(1),
(2) Date: Mar. 1, 2021

(87) PCT Pub. No.: WO2020/049294
PCT Pub. Date: Mar. 12, 2020

(65) Prior Publication Data
US 2021/0188902 A1    Jun. 24, 2021

(30) Foreign Application Priority Data
Sep. 4, 2018 (GB) .................. 1814356

(51) Int. Cl.
*C07K 1/14* (2006.01)
*G01N 33/68* (2006.01)
(Continued)

(52) U.S. Cl.
CPC ......... *C07K 1/145* (2013.01); *G01N 33/6848* (2013.01); *H01J 49/0031* (2013.01); *H01J 49/165* (2013.01)

(58) Field of Classification Search
CPC . C07K 1/145; G01N 33/6848; H01J 49/0031; H01J 49/165
See application file for complete search history.

(56) References Cited

FOREIGN PATENT DOCUMENTS

| EP | 1666486 A1 | 6/2006 |
|---|---|---|
| WO | 2010/000713 A1 | 1/2010 |

(Continued)

OTHER PUBLICATIONS

Matar-Merheb et al., Structuring detergents for extracting and stabilizing functional membrane proteins. PLoS One. Mar. 31, 2011;6(3):e18036, 10 pages.

(Continued)

*Primary Examiner* — Jill A Warden
*Assistant Examiner* — Michael Stanley Gzybowski
(74) *Attorney, Agent, or Firm* — McCarter & English, LLP; Wei Song

(57) ABSTRACT

A method of detecting a protein by mass spectrometry comprises: providing a solution comprising a dendritic detergent and a protein; providing a mass spectrometer comprising a nanoelectrospray ionisation source, a mass analyser and a detector; vaporising the solution using the nanoelectrospray ionisation source; ionising the protein; resolving the ionised protein using the mass analyser; and detecting the resolved protein using the detector. A method of extracting a membrane protein from its native membrane (Continued)

comprises: providing a membrane protein in its native membrane; contacting the membrane protein with a dendritic detergent. Dendritic detergents for use in the methods are also provided.

20 Claims, 11 Drawing Sheets

(51) Int. Cl.
*H01J 49/00* (2006.01)
*H01J 49/16* (2006.01)

(56) References Cited

FOREIGN PATENT DOCUMENTS

WO 2017/149294 A1 9/2017
WO 2018/154318 A1 8/2018

OTHER PUBLICATIONS

European Office Action for Application No. 19769553.9, dated Aug. 21, 2023, 7 pages.
Anatrace, NG311—Octyl Glucose Neopentyl Glycol. Retrieved online at: https://www.anatrace.com/Products/Detergents/NG-CLASS/NG311. 2 pages, (2019).
Gupta et al., Identifying key membrane protein lipid interactions using mass spectrometry. Nat Protoc. May 2018; 13 (5):1106-1120.
Laganowsky et al., Mass spectrometry of intact membrane protein complexes. Nat Protoc. Apr. 2013;8(4):639-51.
Landreh et al., Effects of Detergent Micelles on Lipid Binding to Proteins in Electrospray Ionization Mass Spectrometry. Anal Chem. Jul. 18, 2017;89(14):7425-7430.
Letts et al., Purification of Ovine Respiratory Complex I Results in a Highly Active and Stable Preparation. J Biol Chem. Nov. 18, 2016;291(47):24657-24675.
Liu et al., Affinity Enhancement by Ligand Clustering Effect Inspired by Peptide Dendrimers-Shank PDZ Proteins Interactions. PLoS One. Feb. 26, 2016;11(2):e0149580, 12 pages.
Urner et al., Exploring the Potential of Dendritic Oligoglycerol Detergents for Protein Mass Spectrometry. J Am Soc Mass Spectrom. Jan. 2019;30(1):174-180.
Urner, Oligoglycerol Detergents for Native Mass Spectrometry of Membrane Proteins. Inaugural-Dissertation to obtain the academic degree Doctor rerum naturalium. Submitted to the Department of Biology, Chemistry and Pharmacy of Freie Universitat Berlin. 169 pages, (2018).
International Search Report and Written Opinion for Application No. PCT/GB2019/052462, dated Nov. 15, 2019, 12 pages.
Great Britain Office Action for Application No. GB1814356.0, dated Mar. 15, 2019, 5 pages.

DENDRITIC DETERGENTS FOR THE ANALYSIS OF PROTEINS BY MASS SPECTROMETRY

CROSS-REFERENCE TO RELATED APPLICATIONS

This application is a U.S. national stage filing, under 35 U.S.C. § 371(c), of International Application No. PCT/GB2019/052462, filed on Sep. 4, 2019, which claims priority to United Kingdom Patent Application No. 1814356.0, filed on Sep. 4, 2018.

FIELD OF THE INVENTION

The present invention relates to detergents and their use in methods for analysing proteins. More particularly, the present invention relates to dendritic detergents and their use in methods for extracting proteins from their native membranes, as well as methods for detecting proteins by mass spectrometry. The proteins may be analysed in the form of complexes with ligands such as lipids and therapeutic agents.

BACKGROUND TO THE INVENTION

Membrane proteins are responsible for a wide range of biological functions. Some of the most prevalent human diseases, including some cancers, result from their dysfunction. Despite representing around a third of the human genome, membrane proteins represent targets for more than half of all current therapeutic agents.

Membrane proteins have large hydrophobic surface regions and are known to be difficult to handle in solution upon extraction from the native lipid bilayer environment. Their extraction is usually achieved by amphiphilic molecules such as detergents, which comprise a hydrophilic (water-soluble) and a hydrophobic (water-insoluble) portion. The bipolar character of amphiphiles is responsible for their ability to shield the hydrophobic surfaces of membrane proteins. This enables protein-detergent complexes to be stable in solution upon removal of the membrane environment, which is crucial for the analysis of their structure by biophysical techniques.

As a significant biological target in disease and cancer, their study by traditional structural biology approaches, such as X-ray crystallography and nuclear magnetic resonance, has been frustrated by limitations relating to their expression and solubility. Furthermore, X-ray analysis, in the majority of cases, has been limited by crystallographic resolution hindering the assignment of bound moieties.

In contrast to classical structural biology methods, mass spectrometry (MS) of intact complexes, sometimes referred to as "native MS", is a rapid and sensitive technique that can provide invaluable information on protein complexes, such as specifically bound small molecules. MS of intact soluble membrane proteins has emerged as a powerful technique to study the stoichiometry, structure-function and dynamics of protein assemblies. The technique has also been used to study membrane protein complexes, where it has already revealed subunit stoichiometries and specific phospholipid interactions.

Membrane protein MS is normally performed using a detergent micelle in which the protein is contained. The membrane protein may be prepared by buffer exchange of the purified protein into an MS-compatible buffer supplemented with the detergent. The micellar solution is then ionized by means of nanoelectrospray and transmission into the mass spectrometer.

Detergents that are suitable for native MS ideally maintain the structure of a chosen membrane protein in solution, are tolerated by nESI and provide the ability to obtain a mass spectrum of a membrane protein. Chemical properties of a detergent are important for the gas phase properties of membrane protein ions monitored by MS techniques since they can affect: i) the ease of the detergent removal in the gas phase, ii) average charge state ($z_{ave}$) of the protein in the gas phase upon detergent removal and iii) the ability to detect ligands such as lipids bound to membrane protein complexes.

Non-ionic detergent families are often used to form micellar solutions for use in MS, as high concentrations of non-ionic detergents can be tolerated more readily during the electrospray process. Saccharide detergents are a family of non-ionic detergents. Glucoside and maltoside detergents, such as octyl ß-D-glucopyranosid, n-decyl ß-D-maltoside and n-dodecyl ß-D-maltoside, are commonly used in structural biology and can maintain folded states of membrane proteins upon extraction in solution, and so they are considered as detergents that provide commonly a "soft" solution environment for membrane proteins. Whilst these detergents are compatible with nESI, the energy required for the removal of saccharide detergents in the gas phase and the $z_{ave}$ of the delivered membrane protein ions are comparatively high. This causes commonly unintended unfolding or dissociation of the protein structure. Saccharide detergents are therefore commonly designated as "harsh" in terms of the gas-phase conditions applied to achieve the detergent removal.

Other non-ionic detergents such as polyoxyethylene glycols have also been used in MS techniques, as well as some zwitteronic detergents. Polyethylenglycol and amine oxide detergents, such as tetraethylene glycol monooctyl ether or lauryldimethylamine N-oxide, have charge reducing properties resulting in low $z_{ave}$ enabling them to be removed at lower activation energies compared to saccharide detergents. However, the solution environment of these detergents is considered "harsh" for proteins. This means that ligands may dissociate from a protein, including lipids which can be crucial from preserving the native protein structure.

There exists a need for a detergent family which may be used for extracting and stabilising membrane proteins in solution, but which may also be used for carrying out MS methods for detecting proteins, i.e. a detergent family which can provide both a "soft" solution environment and a "soft" gas-phase environment. There is also a need for a detergent family whose properties can be fine-tuned, for instance to enable proteins to be extracted and analysed using MS in an unbound (apo) state or in a ligand-bound state, and/or to enable the gas-phase charge state of the protein to be controlled.

SUMMARY OF THE INVENTION

According to a first aspect of the invention there is provided a method of detecting a protein by mass spectrometry, wherein the method comprises:
(a) providing a solution comprising a dendritic detergent and a protein;
(b) providing a mass spectrometer comprising a nano-electrospray ionisation source, a mass analyser and a detector;

(c) vaporising the solution using the nanoelectrospray ionisation source;
(d) ionising the protein;
(e) resolving the ionised protein using the mass analyser; and
(f) detecting the resolved protein using the detector;
wherein the dendritic detergent is a non-ionic detergent comprising a dendritic head group linked to a hydrophobic tail, the dendritic head group comprising a branched alkyl group in which up to 1 in 2 carbon atoms may be replaced with an oxygen or nitrogen, provided that the dendritic head group comprises at least 4 hydroxyl groups.

In a further aspect, a method of extracting a membrane protein from its native membrane is also provided, wherein the method comprises:
  i. providing a protein in its native membrane;
  ii. contacting the protein with a dendritic detergent;
wherein the detergent forms a detergent aggregate in which the membrane protein is contained, the dendritic detergent being as defined herein.

In further aspects, a dendritic detergent as defined herein is provided, as is a solution comprising a dendritic detergent and a protein.

Use of a dendritic detergent as defined herein, or a solution as defined herein, for the detection of a protein by mass spectrometry is provided in a yet further aspect.

DESCRIPTION OF VARIOUS EMBODIMENTS

Definitions

Figure 1:
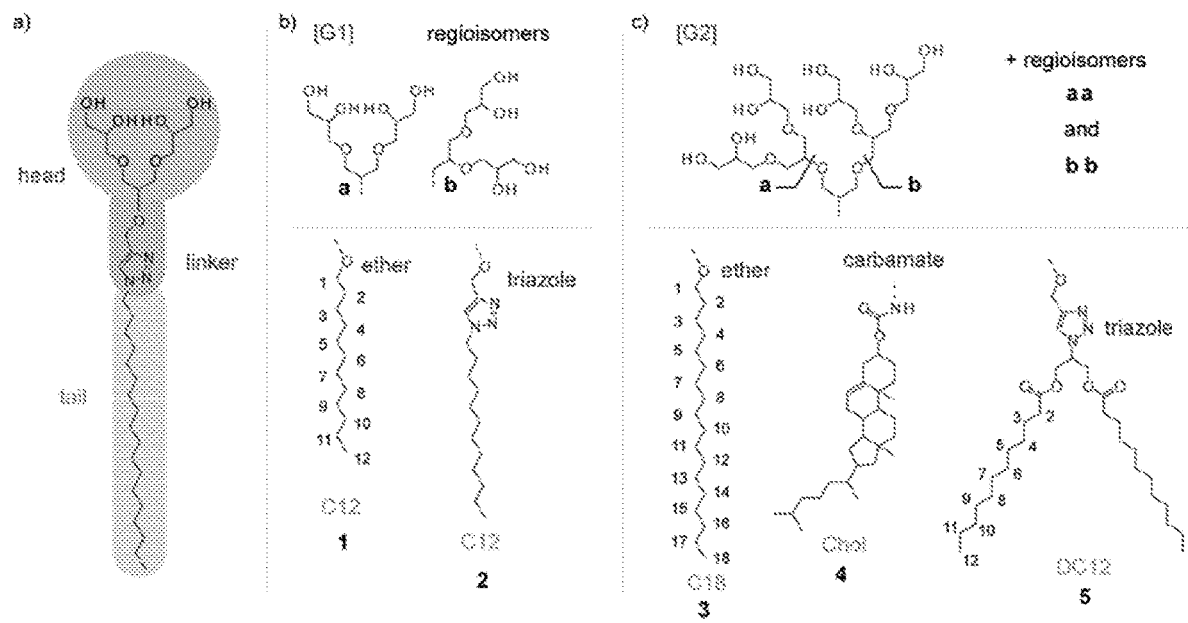
FIG. 1 shows the structure of dendritic detergent batches that were used to carry out experiments on membrane proteins. Specifically, the figure shows: a) the principal structure of the dendritic detergents used in the present invention consisting of a water-soluble head, a hydrophobic tail and a linker. Dendritic detergents based on b) first-generation "[G1]" or c) second-generation [G2] dendritic triglycerol are composed of different head group regioisomers (top), linker and tail structures (bottom).

For the purposes of the present invention, the following terms as used herein shall, unless otherwise indicated, be understood to have the following meanings.

The term "detergent" as used herein refers to a substance which lowers the surface tension of the medium in which it is dissolved, and/or the interfacial tension with one or more other phases. Detergents are generally amphipathic molecules, comprising both hydrophilic and hydrophobic groups, and may be anionic, cationic, non-ionic or zwitterionic unless otherwise specified.

The term "dendritic" as used herein refers to a molecular structure which is repetitively branched. At least one branch point is typically introduced with each generation (i.e. each layer) of growth. The same molecular building block is preferably used in each generation of growth, though this is not necessarily the case. Where there is more than one location on a molecular building block for attachment to the previous/subsequent layer, then regioisomers may form.

The term "hydrophobic" as used herein refers to groups which associate with one another in an aqueous environment. Hydrophobic groups are non-polar by nature.

The term "branch point" as used herein refers to a part in a molecular structure in which a carbon atom is bonded to at least 3 other non-hydrogen atoms, and each of the neighbouring 3 non-hydrogen atoms is in turn bonded to a further non-hydrogen atom. Thus, where a carbon atom is bonded to 2 other carbon atoms and a hydroxyl group, this does not represent a "branch point" since the oxygen in the hydroxyl group is not bonded to any further non-hydrogen atoms.

The term "polyol" as used herein refers to a molecule containing at least two, and preferably at least 3 hydroxyl groups.

The term "hydrocarbyl" as used herein refers to a group that consists only of carbon and hydrogen. Hydrocarbyl groups include straight chain and branched groups, cyclic and acyclic groups, and saturated and unsaturated groups. The term embraces groups which may contain a mixture of cyclic, acyclic, saturated and unsaturated groups. Unless otherwise specified, hydrocarbyl groups are unsubstituted and, as such, consist solely of carbon and hydrogen atoms. Preferred hydrocarbyl groups include alkyl, alkenyl, alkynyl and aryl groups which are described further below. The term "hydrocarbylene" as used herein refers to divalent groups.

The term "alkyl" as used herein refers to a saturated group which may be straight chain or branched, and cyclic or acyclic. The term embraces groups which are cycloalkyl groups, and groups which comprise cyclic and acyclic alkyl groups. Unless otherwise specified, alkyl groups are unsubstituted and, as such, consist solely of carbon and hydrogen atoms. The term "alkylene" refers to divalent groups.

The term "cycloalkyl" as used herein refers to a cyclic alkyl group. The term embraces monocyclic groups and polycyclic groups including fused rings structures and bridged ring systems. In some embodiments, cycloalkyl groups contain 3 to 20 carbon ring atoms. Cycloalkyl groups also include rings to which straight or branched chain acyclic alkyl groups as defined above are attached. Unless otherwise specified, cycloalkyl groups are unsubstituted and, as such, consist solely of carbon and hydrogen atoms. The term "cycloalkylene" refers to divalent groups.

The term "alkenyl" as used herein refers to an alkyl group, e.g. as described above, but which comprises at least one carbon-carbon double bond. Thus, the term embraces straight chain and branched alkenyl groups, as well as non-aromatic cycloalkenyl groups including polycyclic, such as fused ring and bridged ring, structures. Alkenyl groups are preferably, but not necessarily, bonded to the rest of a molecule through a carbon which forms part of a double bond. Unless otherwise specified, alkenyl groups are unsubstituted and, as such, consist solely of carbon and hydrogen atoms. The term "alkenylene" refers to divalent groups.

The term "alkynyl" as used herein refers to an alkyl group, e.g. as described above, but which comprises at least one carbon-carbon triple bond. Thus, the term embraces straight chain and branched alkynyl groups. Alkynyl groups are preferably, but not necessarily, bonded to the rest of a molecule through a carbon which forms part of a triple bond. Unless otherwise specified, alkynyl groups are unsubstituted and, as such, consist solely of carbon and hydrogen atoms. The term "alkynylene" refers to divalent groups.

The term "heterocyclyl" as used herein refers to an aromatic or non-aromatic ring system in which one or more ring members is a heteroatom such as, but not limited to, N, O, and S. A heterocyclyl ring may include one or more double bonds, and so a heterocyclyl group can be a cycloheteroalkyl or a heteroaryl group or, if polycyclic, any combination thereof. In some embodiments, heterocyclyl groups include 3 to 20 ring members. The term "heterocyclyl group" includes polycyclic ring systems containing a heteroatom in the ring, and includes fused ring species including those comprising fused aromatic and non-aromatic groups. Unless otherwise specified, heterocyclyl groups are unsubstituted. The term "heterocyclylene" refers to divalent groups.

The term "cycloheteroalkyl" as used herein refers to a cycloalkyl group, e.g. as described above, but in which one or more ring members is a heteroatom such as, but not limited to, N, O, and S. Thus, the term embraces polycyclic, such as fused ring and bridged ring, structures. In some embodiments, cycloheteroalkyl groups include 3 to 20 ring members. Unless otherwise specified, cycloheteroalkyl groups are unsubstituted. The term "cycloheteroalkylene" refers to divalent groups.

The term "heteroaryl" as used herein refers to an aromatic ring system in which one or more ring members is a heteroatom such as, but not limited to, N, O, and S. In some embodiments, heteroaryl groups include 5 to 20 ring members. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Unless otherwise specified, heteroaryl groups are unsubstituted. The term "heteroarylene" refers to divalent groups.

The term "substituted" as used herein in connection with a chemical group means that one or more (e.g. 1, 2, 3, 4 or 5) of the hydrogen atoms in that group are replaced independently of each other by a corresponding number of substituents. It will, of course, be understood that the one or more substituents may only be at positions where they are chemically possible, i.e. that any substitution is in accordance with permitted valence of the substituted atom and the substituent and that the substitution results in a stable compound. The term is contemplated to include all permissible substituents of a chemical group or compound.

Dendritic Detergents

The dendritic detergents used in the present invention are non-ionic detergents comprising a dendritic head group linked to a hydrophobic tail. The dendritic detergent preferably has the formula (1):

where: D represents the dendritic head group;
L represents a linking group; and
Hy represents the hydrophobic tail.

The dendritic head group comprises:
a branched alkyl group in which up to 1 in 2 carbon atoms may be replaced with an oxygen or nitrogen, provided that the dendritic head group comprises at least 4 hydroxyl groups.

The branched alkyl group may comprise from 1 to 20 branch points, preferably from 1 to 10 branch points, and more preferably from 1 to 5 branch points.

The branched alkyl group is preferably free from cyclic alkyl groups, i.e. it is an acyclic alkyl group.

The branched alkyl group preferably contains up to 2 in 5 carbon atoms replaced with an oxygen or nitrogen. The branched alkyl group may contain at least 1 in 10, preferably at least 1 in 6, and more preferably at least 1 in 4 carbon atoms replaced with an oxygen or nitrogen. Thus, the branched alkyl group may contain from 1 in 6 to 1 in 2, and more preferably from 1 in 4 to 2 in 5 carbon atoms replaced with an oxygen or nitrogen. Preferably any carbon atoms that are replaced in the dendritic head group are replaced with an oxygen atom.

Terminal or non-terminal carbon atoms may be replaced with an oxygen or nitrogen in the branched alkyl group, provided that the dendritic head group comprises at least 4 hydroxyl groups. In other words, at least 4 terminal carbon atoms are replaced with an oxygen. It will be appreciated that a terminal carbon atom is the carbon in the group —CH$_3$. In some embodiments, both terminal and non-terminal carbon atoms are replaced with an oxygen or nitrogen.

The dendritic head group may comprise up to 50, preferably up to 20 and more preferably up to 10 hydroxyl groups. In embodiments, each terminal carbon is replaced with an oxygen.

It will be appreciated that, when a carbon atoms is described as replaced by oxygen, that two hydrogen atoms will also be lost with the carbon atom. Thus, where a carbon atom is replaced with oxygen in the group —CH$_2$— then the group becomes —O—, and where a carbon atom in the group —CRH$_2$ is replaced with oxygen, then the group becomes —OR. Similarly, where a carbon atom is described as replaced by nitrogen, one hydrogen atom will also be lost with the carbon atom. So, where a carbon atom is replaced with nitrogen in the group —CRH— then the group becomes —NR—, and where a carbon atom in the group —CR$_2$H is replaced with nitrogen, then the group becomes —NR$_2$.

The dendritic head group may be derived from a polyol. In particularly preferred embodiments, the dendritic head group is derived from glycerol. Preferably the dendritic head group comprises an oligopolyol. For instance, the dendritic head group may comprise an oligopolyol containing at least 2, and preferably at least 3 polyol monomers. The dendritic head group may comprise an oligopolyol containing up to 50, preferably up to 30, and more preferably up to 15 polyol monomers. Thus, the dendritic head group may comprise an oligopolyol containing from 2 to 50, preferably from 3 to 30 and more preferably from 3 to 15 polyol monomers.

The dendritic head group may have a structure selected from:

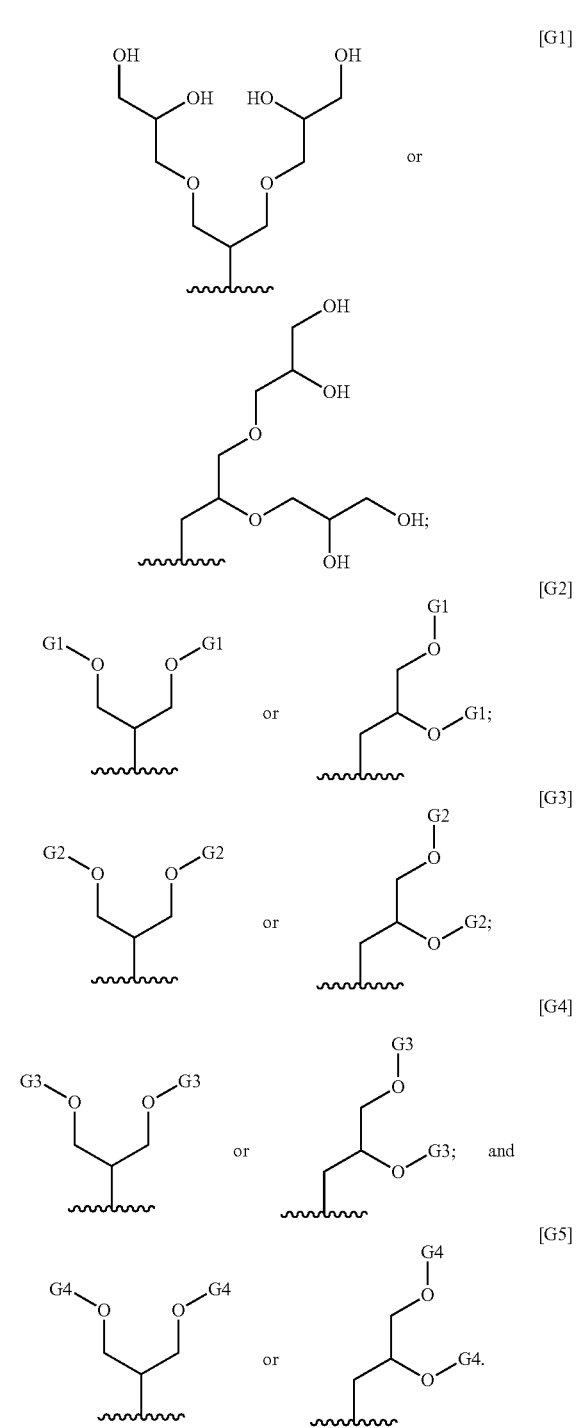

It will be appreciated that the two structures shown above as belonging to the first generation of dendritic head groups [G1] represents regioisomers of one another. Further regioisomerism may be introduced with each subsequent generation of growth.

Where a dendritic head group contains a reference to an earlier dendritic head group, each of the earlier dendritic head groups may be either of the regioisomers depicted.

For instance, where [G2] is:

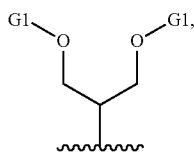

it may take one of the following three regioisomer structures:

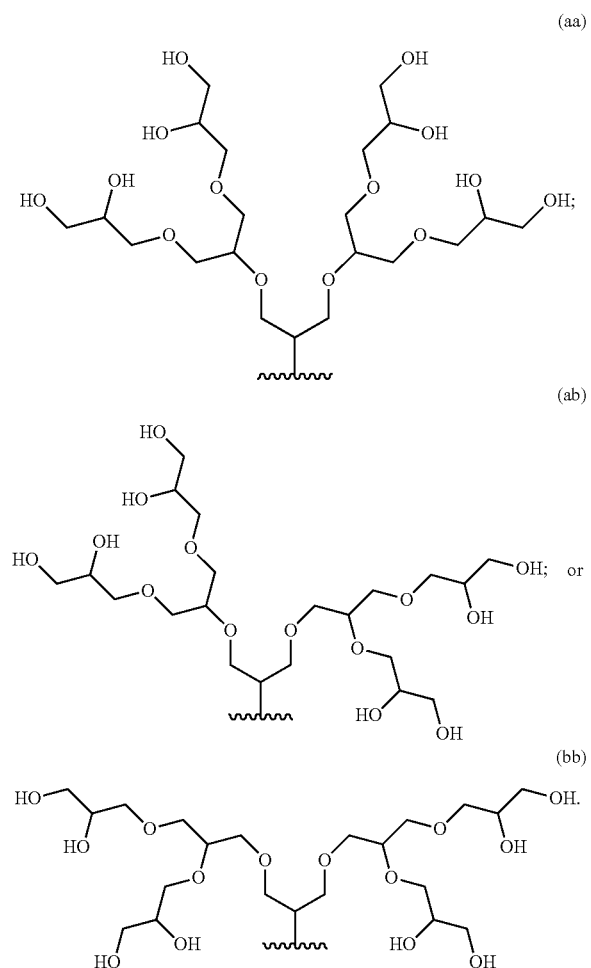

It will be understood that the second generation of dendritic head groups [G2] contains 6 different regioisomers in total (i.e. 2 structures for [G2], each embracing 3 regioisomers), the third generation of dendritic head groups [G3] contains 42 different regioisomers in total, and so on.

The dendritic detergent used in the present invention may be used in the form of a mixture of dendritic detergents having head groups which are regioisomers of one another. For instance, the mixture may comprise a first dendritic detergent and a second dendritic detergent, the head groups of the first and second dendritic detergents being regioisomers of one another. The use of a mixture of regioisomers is believed to give improved levels of membrane protein extraction from a native membrane.

In embodiments, the dendritic detergent is in the form of a mixture of dendritic detergents having head groups which represent at least n+1 regioisomers of one another, where n is the generation of the dendritic detergent. Thus, a first generation dendritic detergent may be used in the form of a mixture of dendritic detergents having head groups which represent at least 2 regioisomers of one another. A second generation dendritic detergent may be used in the form of a mixture of dendritic detergents having head groups which represent at least 3 regioisomers of one another. Each regioisomer is preferably present in the mixture of dendritic detergents in a molar amount of greater than 5%, e.g. greater than 20%.

In alternative embodiments, the dendritic detergent may be used in the form of a single regioisomer.

Preferred dendritic head groups are selected from [G1], [G2] and [G3] and, more preferably, from [G1] and [G2].

It will be appreciated that dendritic detergents such as those above may also be used in the form of a mixture of dendritic detergents of different generations.

Figure 12:
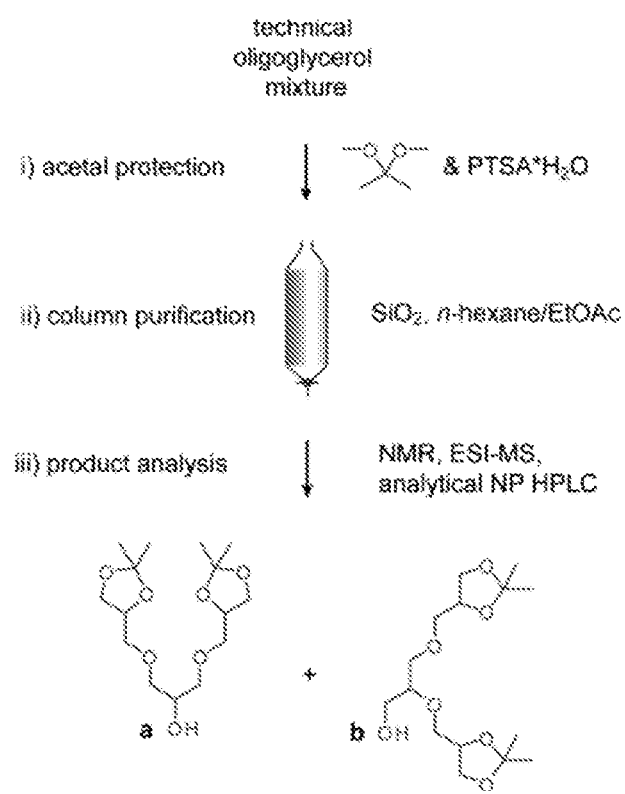
FIG. 12 shows a method for preparing a mixture of acetal-protected first generation dendritic head groups, [pG1]-OH, from a technical oligoglycerol mixture and for isolating the individual regioisomers.
Figure 13:
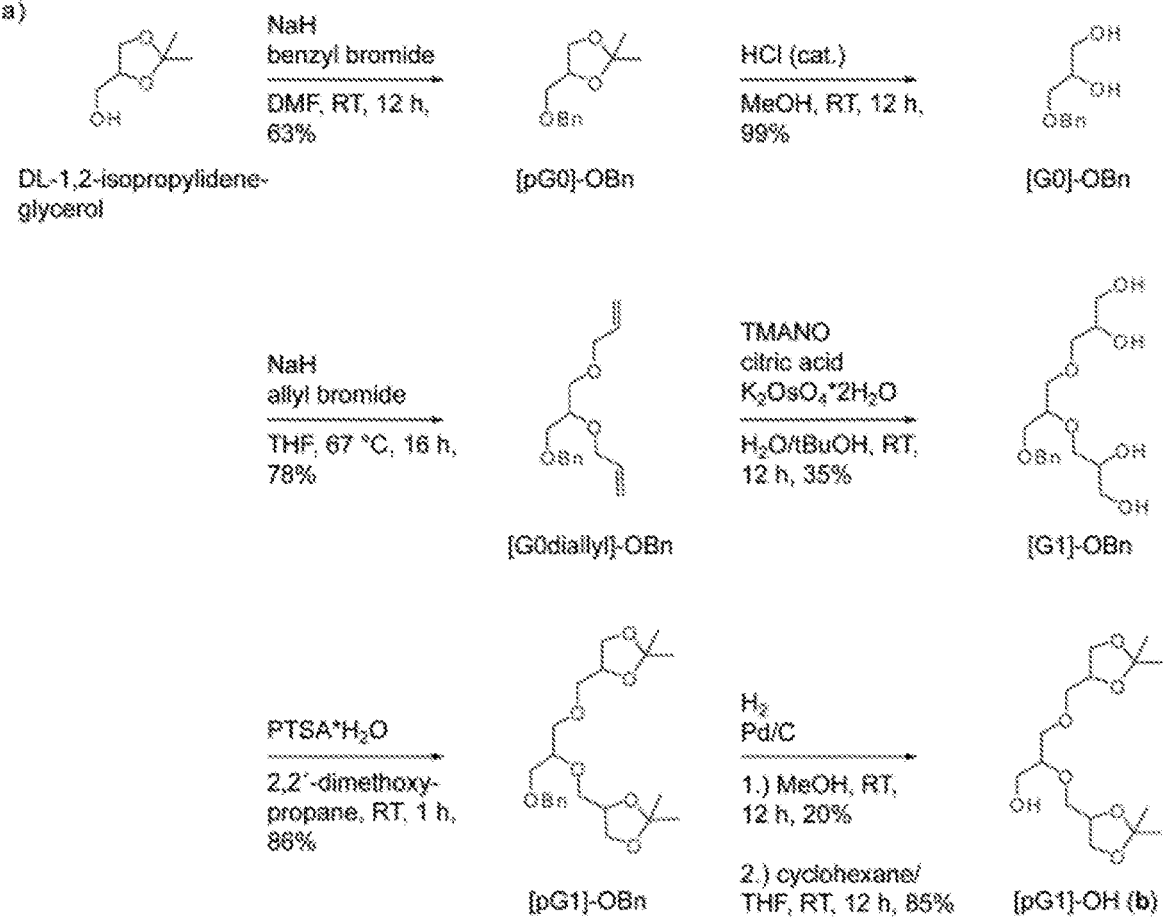
FIG. 13 shows methods for preparing individual acetal-protected first generation dendritic head group regioisomers, [pG1]-OH.
Figure 13:
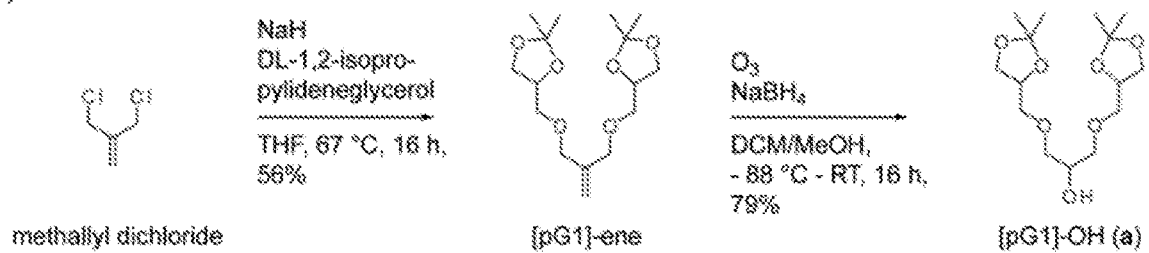

The dendritic head group may be prepared by a method as described in Wyszogrodzka et al. Chem. Eur. J. 2008, 14, 9202-9214, the contents of which is incorporated herein by reference. For instance, first generation dendritic head groups [G1] may be prepared by a method in which a mixture of oligoglycerols (available commercially as technical oligoglycerol mixtures) are reacted with a reagent (e.g. 2,2'-dimethoxypropane) to give a acetal-protected head groups, [pG1]-OH, in the form of a mixture. If desired, these may then be separated by chromatography into individual regioisomers (see FIG. 12). Alternatively, individual acetal-protected regioisomers may be prepared synthetically, e.g. using the scheme depicted in FIG. 13. Subsequent generations of dendritic head group may be prepared by reacting acetal-protected first generation head groups, [pG1]-OH, with a reagent, e.g. methallyl dichloride. Acetal protecting groups may be removed using conventional deprotection methods. Deprotection will typically be carried out once the dendritic head group has been attached to the linking group and hydrophobic tail.

The linking group may be selected from: hydrocarbylene, heterocyclylene, O, S, NR', NR'—O, C(O)NR', OC(O)NR', OC(O)O, NR'C(O)NR', NR'C(S)NR', C(NR')NR', C(O), S(O)$_2$, S(O), S(O)$_2$O, S—S, CR'=N, CR'=N—NR', C=N—NR'C(O), and combinations of up to three of these groups, where each R' is independently selected from H, C$_{1-4}$ alkyl and C$_{1-4}$ alkoxy.

It will be appreciated that these groups may be used to link the head group and the hydrophibic tail of the dendritic detergent in any orientation. For instance, the group NR'—O may be used as: D-NR'—O-Hy or as D-O—NR'-Hy.

Suitable hydrocarbylene groups include alkylene, alkenylene, alkynylene and arylene groups, preferably C$_{1-6}$ alkylene, C$_{2-6}$ alkenylene, C$_{2-6}$ alkynylene and C$_{5-10}$ arylene, and more preferably C$_{1-3}$ alkylene, C$_{2-3}$ alkenylene, C$_{2-3}$ alkynylene and C$_{5-6}$ arylene. The alkylene, alkenylene and alkynylene groups are preferably acyclic.

Suitable heterocyclylene groups include 5-10 membered, and preferably 5-6 membered, heterocyclylene rings containing 1 or 3 heteroatoms. The heteroatoms in the heterocyclylene rings are preferably selected from O, N and S, and more preferably from O and N. The heterocyclene groups may be selected from heteroalkylene and heteroarylene groups, and preferably from heteroarylene groups. Preferred groups include those derived from triazole, imidazole, oxazole and pyridine, i.e. divalent forms of these groups.

R' is preferably selected from H, $C_{1-2}$ alkyl and $C_{1-2}$ alkoxy, and more preferably from H and $C_{1-2}$ alkyl.

The linking group is preferably selected from: O, O—$C_{1-2}$ alkylene-aryl and OC(=O)NR', and more preferably from O, O—CH$_2$-triazolyl and OC(=O)NH. O—CH$_2$-triazolyl is preferably joined to the dendritic head group via the oxygen, and OC(=O)NH is preferably joined to the dendritic head group via the nitrogen. The group O—CH$_2$-triazolyl preferably has the structure:

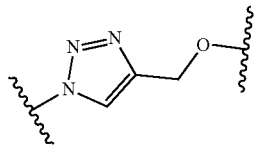 [SMILES: *OCc1cn(*)nn1]

The dendritic detergents comprise a hydrophobic tail. It is this group which is believed to associate with hydrophobic portions on the surface of proteins.

The hydrophobic tail may be a $C_{6-100}$ alkyl group in which one or more methylene groups may be independently replaced by a unit selected from: $C_{2-6}$ alkenylene, $C_{2-6}$ alkynylene, $C_{5-10}$ arylene, O, S, NR'', NR''—O, C(O)NR'', OC(O)NR'', OC(O)O, NR''C(O)NR'', NR''C(S)NR'', C(NR'')NR'', C(O), S(O)$_2$, S(O), S(O)$_2$O, S—S, CR''=N, CR''=N—NR'', C=N—NR''C(O), where each R'' is independently selected from H, $C_{1-4}$ alkyl and $C_{1-4}$ alkoxy.

Preferably, the hydrophobic tail is a $C_{8-50}$ alkyl group, such as a $C_{10-30}$ alkyl group, in which one or more methylene groups may be independently replaced by a unit as described above.

The hydrophobic tail may have up to 6 methylene groups, preferably up to 4 methylene groups, and more preferably up to 2 methylene groups replaced by a unit as described above.

The hydrophobic tail preferably comprises a terminal acyclic alkyl group having at least 6 carbon atoms. This group may be branched or unbranched but, where it is branched, it preferably only comprises methyl side chains, e.g. 1 to 4, e.g. 1 or 2, methyl side chains.

R'' is preferably selected from H, $C_{1-2}$ alkyl and $C_{1-2}$ alkoxy, and more preferably from H and $C_{1-2}$ alkyl.

In some embodiments, the hydrophobic tail may be lipid-like. For instance, the hydrophobic tail may be derived from a lipid. Hydrophobic tails derived from a lipid include those derived from sterols, such as cholesterol. Lipid-like hydrophobic tails may also be structurally similar to lipids, such as fatty acids. For example, a lipid-like hydrophobic tail may comprise at least one group having the structure —OC(O)—$C_{10-30}$ acyclic alkyl.

The hydrophobic tail is preferably selected from $C_{10-30}$ acyclic alkyl, CH$_x$(CH$_2$—OC(O)—$C_{10-30}$ acyclic alkyl)$_y$, where x is selected from 1 or 2 and x+y=3, and cholesterol. A cholesterol hydrophobic tail has the structure:

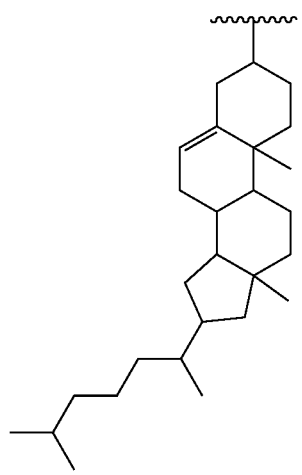 [SMILES: *C1CCC2(C)C(=CCC3C4CC(C(C)CCCC(C)C)CC4(C)CCC32)C1]

The dendritic detergent may be prepared using standard techniques in the art, e.g. using standard addition reactions between the dendritic head group, the linking group and the hydrophobic tail. For instance, suitable techniques are disclosed by R. Haag et al. in WO 2010/000713 and in Thota et al., Chem. Commun. 2015, 51, 8648-8651.

The present invention is based, in part, on the discovery that the properties of the family dendritic detergents defined herein can be fine-tuned to suit particular uses.

In methods of detecting a protein by mass spectrometry:
Where detection of protein-lipid binding is desired, dendritic detergents having at least 2 branch points (e.g. [G2] dendritic detergents) are preferred. Dendritic detergents having lipid-like hydrophobic tails (e.g. a hydrophobic tail derived from a sterol such as cholesterol or structurally similar to a fatty acid) are also preferred. Most preferred are dendritic detergents having at least 2 branch points and a lipid-like hydrophobic tail. Where the protein is a membrane protein, the protein is preferably extracted from its native membrane using these detergents, since the bound lipids are preferably co-purified from the native membrane.

Where detection of a protein in its apo state is desired, dendritic detergents having just one branch point, e.g. a [G1] head group, are preferred. Dendritic detergents having a $C_{10-30}$ acyclic alkyl hydrophobic tail are also preferred. Most preferred are detergents having just one branch point and a $C_{10-30}$ acyclic alkyl hydrophobic tail.

Where a reduced protein charge state is desired, a basic linking group is preferred. Groups which exhibit high gas-phase basicity, such as heteroarylene groups, are particularly preferred.

In methods of extracting a membrane protein from its native membrane:
Dendritic detergents having just one branch point, e.g. a [G1] head group, are preferred, particularly when used in the form of a mixture of different regioisomers.

Detecting a Protein Using Mass Spectrometry

The dendritic detergents may be used in a method of detecting a protein by mass spectrometry. The method involves the use of a solution comprising a non-ionic detergent as defined herein and a protein. The solution is vaporised using a nanoelectrospray ionisation source. The protein is ionised, and subsequently resolved and detected.

Proteins may be composed of one (mono) or more (multi) associated polypeptide chains. Thus, the protein may be a monomeric or a multimeric protein, for example an oligomeric membrane protein. Oligomeric proteins include both homooligomeric (identical polypeptide chains) and heterooligomeric (different polypeptide chains) proteins.

In an embodiment, the protein has a molecular weight of from about $10^3$ Daltons to about $10^{12}$ Daltons, e.g. from about $10^3$ Daltons to about $10^6$ Daltons.

The protein that is detected may be a membrane protein or a soluble protein, and is preferably a membrane protein.

Membrane proteins can be grouped into integral membrane proteins and peripheral membrane proteins. Integral membrane proteins may have one or more segments embedded within a membrane and may be bound to the lipid bilayer. Peripheral membrane proteins may be temporarily associated with the lipid bilayer and/or integral membrane proteins. In an embodiment, the membrane protein is an integral membrane protein.

In an embodiment, the membrane protein is an integral membrane protein selected from G protein-coupled receptors (GPCRs), membrane transporters, membrane channels, ATP-binding cassette transporters (ABC-transporters), proton driven transporters, solute carriers and outer membrane proteins (OMPs). In specific examples, the membrane protein is selected from aquaporin Z (AqpZ); ammonia channel (AmtB), multi-antimicrobial extrusion protein (MATE), outer membrane protein F (OmpF), and neurotensin receptor 1 (NTSR1). The membrane proteins may be tagged, e.g. with polyhistidine-tag, and/or they may be fused to a further protein, e.g. a green fluorescent protein (GFP) or a maltose-binding protein (MBP).

Soluble proteins are present outside of a cellular membrane in organisms, e.g. in the cytoplasm.

In embodiments, the soluble protein exhibits amphiphilic character. In specific examples, the soluble protein is 3-lactoglobulin (BLG).

The solution comprising a dendritic detergent and a protein may be provided by known methods. Methods for the purification and expression of proteins are known in the art. By way of example, Barrera et al., Nat. Methods 2009, 6, 585-587 describe methods for the purification of MacB, LmrCD, and EmrE. Moreover, Drew et al., Nat. Protoc., 2008, 3, 784-798 describe a GFP fusion construct methodology in which yields in the overexpression and purification of membrane proteins are improved, while Aller et al., Science, 2009, 323, 1718-1722 describe P-glycoprotein expression and purification. Reference may also be made to Zhang et al., Nature, 2015, 520, 317. Proteins may also be commercially available. In order to produce high quality mass spectra, the protein should preferably be relatively pure and homogenous, equivalent to crystallographic-grade material.

Where the protein is a membrane protein, the solution comprising a dendritic detergent and a protein may also be provided by a method in which the membrane protein is extracted from its native membrane. This method is described in greater detail below.

The protein may be in the form of a complex with a ligand. The present methods may therefore be used to detect binding between a protein and a ligand. In particular, a method of the present invention may allow one or more structural characteristics (e.g. stoichiometry) of a protein-ligand complex to be determined, and/or may also be used to detect conformational changes that take place upon binding of a therapeutic agent to the protein.

Binding of the ligand to the protein may be via a non-covalent or a covalent interaction, though will typically be via a non-covalent interaction. In particular, binding of the ligand to the protein may be via intermolecular forces such as ionic bonds, hydrogen bonds and van der Waals forces. Binding of the ligand to the protein may be reversible or irreversible. In an embodiment, the ligand is bound to the protein via a reversible bond.

Ligands with which the protein may be in the form of a complex include one or more of therapeutic agents, lipids, nucleotides and nucleosides.

In some embodiments, the protein may be in the form of a complex with one or more lipids. Particular examples of lipids include, but are not limited to, fatty acids, glycerolipids, glycerophospholipids, sphingolipids, sterol lipids, prenol lipids, saccharolipids and polyketides. Membrane proteins are more likely to be detected in the form of a complex with one or more lipids due to the hydrophobic regions on their surface, as well as the "native" membrane environment from which they are obtained.

In one embodiment, the protein is in the form of a complex with one or more therapeutic agents. These embodiments are particularly preferred when the protein is a membrane protein, since these proteins are key targets for therapeutic agents. The therapeutic agent may be an active compound which, when administered to an organism (human or non-human animal), induces a desired pharmacologic, immunogenic, and/or physiologic effect by local and/or systemic action. Examples of therapeutic agents include, without limitation, drugs, vaccines and biopharmaceutical agents. Thus, therapeutic agents may include small molecule drugs, therapeutic proteins, peptides and fragments thereof (whether naturally occurring, chemically synthesised or recombinantly produced), and nucleic acid molecules (including both double-and single-stranded molecules, gene constructs, expression vectors, antisense molecules and the like). Therapeutic agents may also include substrates, inhibitors, activators, neurotransmitters, agonists and antagonists. The therapeutic agent may be a synthetic or naturally occurring compound. The therapeutic agent may be a drug candidate or other agent suspected of having therapeutic application.

Particular examples of therapeutic agents include, but are not limited to, anti-cancer agents, anti-infective agents (e.g. antibiotics and antiviral agents), analgesic agents, anorexic agents, anti-inflammatory agents, antiepileptic agents, anaesthetic agents, hypnotic agents, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics agents, hormones, nutrients, antiarthritics agents, antiasthmatic agents, anticonvulsants, antihistamines, antinauseants agents, antineoplastic agents, antipruritics agents, antipyretic agents; antispasmodic agents, cardiovascular agents (e.g. calcium channel blockers, beta-blockers, beta-agonists, antiarrhythmic agents, antihypertensive agents, diuretics and vasodilators), central nervous system stimulants; decongestants, hormones, bone growth stimulants, bone resorption inhibitors, immunosuppressive agents, muscle relaxants, psychostimulants, sedatives and tranquilisers. It will be appreciated that this list of therapeutic agents is merely illustrative and should not be considered to be limiting. Many other therapeutic agents are known in the art and may be utilised in a method of the present invention. A detailed description of various therapeutic agents may be found in e.g. Remington's Pharmaceutical Sciences (21st edition, 2005, Mack Publishing Company). The therapeutic agent may exhibit optical isomerism and/or diastereoisomerism. Accordingly, the therapeutic agent may be in the form of a single enantiomer or diastereoisomer, or a mixture (e.g. a racemic mixture) thereof.

In an embodiment, the therapeutic agent has a molecular weight of less than 2000 Daltons, e.g. less than 1500 Daltons, e.g. less than 1000 Daltons, e.g. less than 500 Daltons. In an embodiment, the therapeutic agent is a non-polymeric organic compound having a molecular weight of less than 1000 Daltons, e.g. less than 800 Daltons, e.g. less than 500 Daltons.

In an embodiment, the therapeutic agent is an inhibitor or an activator, e.g. an activator or inhibitor of the protein to which it is bound. In an embodiment, the therapeutic agent is an anti-cancer agent.

A method of the present invention may allow therapeutic agents to be screened. In contrast to indirect methods such as fluorescence or calorimetry, the present method may allow therapeutic agents to be screened directly. In particular, a method may be used to screen for the binding of activators and transporter substrates which are difficult to screen using conventional in vivo methodologies. Moreover, unlike X-ray crystallography, the present methods are not complicated by the inherent structural flexibility of protein-therapeutic agent complexes and may allow the dynamical behaviour of proteins and their interaction with therapeutic agents to be studied.

The protein may be in the form of a complex with more than one ligand. Thus, for instance, a method of the present invention may be used to determine whether the presence of a first ligand affects binding of a second ligand to the protein.

In some embodiments, one or more hydrogen atoms on the protein have been exchanged for an alkali metal cation. Thus the protein in the solution may be an alkali metallated protein. The alkali metal may be selected from sodium and potassium, and is preferably sodium. Other alkali metals could also be used such as rubidium, caesium or francium. The protein may be metallated by introducing alkali metal cations (e.g. approximately 500 µM solution) to the solution in which the dendritic detergent and protein are contained.

The protein may be detected in its metallated form. However, the use of alkali metal cations is preferred because it is believed to facilitate the formation of a protein having a lower charge state ($z_{ave}$) in the gas phase. Without wishing to be bound by theory, it is believed that the dendritic head group of the dendritic detergent associates with the alkali metal cation, facilitating its removal. Thus, the protein is preferably detected in a non-metallated form.

Though in some instances, an alkali metal cation may be added to the protein, in other instances the dendritic detergents of the present invention may be used to improve the resolution of a spectrum when protein samples are contaminated with alkali metal cations, e.g. by reducing peak broadening that is caused by the formation of protein-alkali metal complexes. Alkali metal contaminants are often found in commercial protein batches. This is because they are a common component of salts that are used in protein purification buffers, e.g. sodium chloride, and proteins are often not quantitatively desalted after purification.

The present invention involves the use of a solution in which the dendritic detergent and protein are contained. The dendritic detergent is preferably associated with the protein so that the dendritic detergent may stabilise the protein in the gas phase.

In preferred embodiments, particularly where a membrane protein is used, the solution comprises a detergent aggregate in which the protein is contained, the detergent aggregate being formed by the dendritic detergent. The detergent aggregate is preferably in the form of a micelle (e.g. a substantially spherical micelle or a worm-like micelle), but may also be in the form of a vesicle or a tubular aggregate.

Where the protein is encapsulated in a detergent aggregate for solubilisation, the aggregate is believed to at least partially shield the protein during the electrospray ionisation process. Without wishing to be bound by theory, it is believed that the aggregate may shield the protein during the droplet phase of the electrospray ionisation process and, moreover, may afford at least partial shielding from ionisation of the protein during this process. The detergent aggregate may exert a pressure sufficient to maintain the structure of the protein, thereby minimising the deleterious effects associated with vaporisation and substantially retaining interactions between the protein and any ligand as well as interactions within any subunits of the protein.

The solution will typically comprise a plurality of detergent aggregates containing the protein. The solution may be formed by e.g. incubating the protein in the presence of the detergent.

Preferably, the protein is maintained in the solution in an intact, folded state. This may allow the protein to be detected in its folded, i.e. "native", state. Alternatively, the protein may be present in the solution in a partially folded or unfolded state.

As previously mentioned, the solution may be formed using a single dendritic detergent or a mixture of different dendritic detergents. The solution may also contain one or more detergents in addition to the dendritic detergent(s). Examples of other detergents include non-ionic detergents such as n-dodecyl-D-maltoside, nonylglucoside, glycosides, neopentyl glycols, facade EM, maltosides, glucosides, and mixtures thereof. In an embodiment, the solution does not contain any detergents apart from the dendritic detergent.

In an embodiment, the dendritic detergent is present in the solution at a concentration of from about 100 µM to about 100 mM, e.g. from about 100 µM to about 200 µM. In an embodiment, the protein is present in the solution at a concentration of from about 10 nM to about 1 mM, e.g. from about 100 nM to about 900 nM.

In an embodiment, the molar ratio of the dendritic detergent to the protein is from about 0.5:1 to about 150:1. Where the protein is a soluble protein, then the dendritic detergent is not required to solubilise the protein in the aqueous mass spectrometry environment, and so the dendritic detergent may be used in lower amount, e.g. from about 0.5:1 to about 50:1, e.g. from about 0.75:1 to about 10:1, and more preferably from about 1:1 to about 5:1. However, where the protein is a membrane protein, larger molar ratios of dendritic detergent to protein are preferred, e.g. from 10:1 to 150:1, e.g. from about 30:1 to about 125:1, e.g. from about 50:1 to about 100:1. In a preferred embodiment, the molar ratio of the detergent to the membrane protein is less than or equal to 100:1.

In order to minimise dissociation of the protein and/or precipitation of the protein, the dendritic detergent is preferably present in the solution at a concentration at least equal to, and preferably at two times the critical aggregation concentration (CAC), of the detergent. The CAC of the dendritic detergent may be determined experimentally, e.g. using a dynamic light scattering method. A suitable method is described in the experimental section herein.

Where the protein is in the form of a complex with a therapeutic agent, the micellar solution preferably comprises a molar excess of the therapeutic agent as compared to the protein. In an embodiment, the molar ratio of the therapeutic agent to the protein is at least 2:1, e.g. at least 5:1, e.g. at least 10:1. In an embodiment, the therapeutic agent is present in the solution at a concentration of at least 100 nM, e.g. from 100 nM to 900 nM. Other ligands such as lipids, nucleotides and nucleosides may be in a complex with the protein in its native environment and, as such, will typically not be added to the solution.

The solution may comprise one or more other components. In particular, the solution preferably contains a buffer. Ammonium acetate is particularly preferred in this regard. The concentration of ammonium acetate is preferably at least 150 millimolar. Preferably the pH of the buffer is in the range of from about 5 to about 8. When working with proteins containing His-tags, it may be preferable to use a pH of about 8 to avoid protein insolubility or precipitation which may otherwise occur in lower pH buffered solutions.

Buffer exchange and concentration of the solution may be achieved using suitable techniques and devices known in the art, e.g. using a Micro Bio-Spin @ column (Bio-Rad Laboratories) or a Vivaspin device (GE Healthcare).

The protein is detected using a mass spectrometer comprising a nanoelectrospray ionisation source, a mass analyser and a detector. The mass spectrometer is preferably adapted to transmit and detect ions having mass-to-charge (m/z) ratios in the range of e.g. from about 100 m/z to about 32,000 m/z. Preferably, the mass spectrometer is operated under conditions suitable for maintaining and focusing large macromolecular ions. By way of illustration, and without limitation, the mass spectrometer may be a Synapt HDMS ion-trap-IM-MS instrument (more preferably a G1 instrument) or, preferably, a Q-Exactive hybrid quadrupole-orbitrap mass spectrometer. The resolution provided by such instruments is particularly suited to resolving peaks generated from a complex comprising a protein bound to a ligand.

The nanoelectrospray ionisation source is used to vaporise the solution. Nanoelectrospray ionisation is a technique well known in the art (see e.g. Wilm et al, Anal. Chem. 1996, 68, 1-8; and Wilm et al, Int. J. of Mass Spec. and Ion Proc. 1994, 132, 167-180). The use of nanoelectrospray ionisation allows ions, and in particular highly charged ions, to be generated directly from solution. The formation of highly charged ions may allow the detection of high mass complexes at relatively low mass-to-charge (m/z) ratios. The use of a nanoelectrospray ionisation is also desirable from the point of view of allowing a protein complex, or subunits of a complex, to remain substantially intact. In performing a method of the present invention, it may be preferable to use a nanoflow capillary, e.g. a gold-coated nanoflow capillary, to vaporise the solution.

The solution is preferably vaporised under conditions such that the dendritic detergent is dissociated from the protein. For instance, where the solution comprises detergent aggregates in which the protein is contained, the solution is preferably vaporised under conditions such that the protein is released from the aggregate. It may, however, occasionally be useful to detect a protein bound to one or more dendritic detergent molecules, e.g. in order to study dissociation of the detergent from the protein. The dendritic detergent may be may be dissociated from the protein as a result of collisions between the electrospray and the detergent which serve to disrupt the detergent-protein interactions. Preferably, the vaporisation conditions are selected so that the protein is detected substantially intact. Preferably, the conditions inside the mass spectrometer are selected to rapidly remove the dendritic detergent from the protein.

Ionisation of the protein may occur during the step of vaporising and/or after release of the protein from the detergent. In some instances, portions of the protein, e.g. hydrophilic/cytoplasmic domains, may become ionised prior to release of the protein from the detergent. Typically, ionisation of the protein occurs during and/or after dissociation of the dendritic detergent from the protein.

In an embodiment, release and/or ionisation of the protein occurs in a collision cell present within the mass spectrometer. Release and/or ionisation of the protein may be achieved by adjusting acceleration voltages and/or pressures within the collision cell to remove the detergent while retaining the peaks of the protein.

Mass spectrometer parameters may be optimised for maximal desolvation and detergent removal, while minimising protein activation. In particular, one or more of the following parameters may be optimised: collision voltage, cone voltage, collision gas pressure, collision gas type, and source pressure. Optimisation of parameters may be achieved by first setting the instrument parameters to relatively high activation settings for proteins. Then iteratively, each of the aforementioned four parameters may be adjusted to produce resolved mass spectra while minimizing overactivation of the target protein.

In an embodiment, the mass spectrometer is operated under one or more of the following conditions: (i) a capillary voltage of from about 0.4 to about 3 kV, e.g. from about 1.0 to about 2.0 kV, e.g. from about 1.2 to about 1.8 kV; (ii) a cone voltage of from about 1 to about 240 V, e.g. from about 5 to about 50 V, e.g. from about 100 to about 200 V: (iii) a trap collision energy of from about 0 to about 240 V, e.g. from about 100 to about 220 V, e.g. from about 120 to about 200 V; (iv) a source temperature of from about 0 to about 200° C., e.g. from about 0 to about 50° C., e.g. from about 10 to about 30° C., e.g. about 20° C.; (v) a bias voltage of from about 0 to about 200 V, e.g. from about 40 to about 180 V, e.g. from about 80 to about 160 V; and (vi) a backing pressure of from about 1 to about 8 mBar, e.g. from about 3 to about 6 mBar, e.g. from about 4 to about 5 mBar. In a particular embodiment, the mass spectrometer is operated with a bias voltage of from about 0 to about 200 V, e.g. from about 40 to about 180 V, e.g. from about 80 to about 160 V. In a particular embodiment, the trap collision energy is from about 50 to about 200 V.

In an embodiment, the mass spectrometer is a Synapt HDMS ion-trap-IM-MS instrument (more preferably a G1 or G2 instrument) and is operated under one or more of the following conditions: (i) a capillary voltage of from about 0.4 to about 2.2 kV, e.g. from about 1.0 to about 2.0 kV, e.g. from about 1.2 to about 1.8 kV; (ii) a cone voltage of from about 5 to about 200 V, e.g. from about 100 to about 200 V, e.g. from about 5 to about 50 V: (iii) a trap collision energy of from about 0 to about 240 V, e.g. from about 100 to about 220 V, e.g. from about 120 to about 200 V; (iv) a source temperature of from about 25 to about 40° C., e.g. from about 10 to about 30° C., e.g. about 20° C.; (v) a bias voltage of from about 0 to about 200 V, e.g. from about 40 to about 180 V, e.g. from about 80 to about 160 V; and (vi) a backing pressure of from about 1 to about 8 mBar, e.g. from about 3 to about 6 mBar, e.g. from about 4 to about 5 mBar. In a particular embodiment, the mass spectrometer is operated with a bias voltage of from about 0 to about 200 V, e.g. from about 40 to about 180 V, e.g. from about 80 to about 160 V. In a particular embodiment, the trap collision energy is from about 0 to about 200 V.

In preferred embodiments, a mass spectrometer, e.g. an orbitrap mass spectrometer such as a Q-Exactive hybrid quadrupole-orbitrap mass spectrometer (e.g. available from Thermo Scientific), is operated under one or more of the following conditions: (i) an injection flatapole voltage of about 2.0 to about 8.0 V, e.g. about 4.0 to about 8.0 V, e.g. about 6.0 to about 8.0 V, e.g. 7.9 V; (ii) an inter flatapole lens voltage of about 2.0 to about 7.0 V, e.g. about 4.0 to about 7.0 V, e.g. about 6.0 to about 7.0 V, e.g. 6.9 V; (iii) a bent flatapole voltage of about 2.0 to about 6.0 V, e.g. about 4.0 to about 6.0 V, e.g. about 5.0 to about 6.0 V, e.g. 5.9 V; (iv) a transfer multipole of about 3.0 to about 5.0 V, e.g. about 3.25 to about 4.75 V, e.g. about 3.5 to about 4.5 V, e.g. 4 V; (v) an acceleration voltage in the higher-energy collisional dissociation (HCD) cell of from about 0 to about 250 V, e.g. from about 50 to about 225 V, e.g. from about 100 to about 210 V; (vi) an in-source trapping activation of about 0 V to about 300 V; and (vii) a pressure in the HCD cell of from about $8.0 \times 10^{-10}$ to about $2.0 \times 10^{-9}$ mBar, e.g. from about $8.5 \times 10^{-10}$ to about $1.5 \times 10^{-9}$ mBar, e.g. from about $9 \times 10^{-9}$ to about $1 \times 10^{-9}$ mBar.

The Q-Exactive mass spectrometer may also be operated under one or more of the following conditions: (viii) transient time of about 20 to about 150 ms, e.g. about 50 to about 125 ms, e.g. about 100 ms; (ix) a noise level parameter of about 2.5 to about 5, e.g. about 3 to about 4, e.g. about 3 to about 3.5, e.g. 3; (x) resolution of about 8,000 to about 140,000, e.g. about 10,000 to about 100,000, e.g. about 15,000 to about 30,000, e.g. about 17,500.

The Q-Exactive mass spectrometer may also be operated under one or more of the following conditions: (xi) a capillary voltage of from about 0.8 to about 2.2 kV, e.g. from about 1.0 to about 2.0 kV, e.g. from about 1.2 to about 1.8 kV; (xii) a source temperature of from about 25 to about 100° C., e.g. from about 10 to about 30° C., e.g. about 20° C.; (xiii) a DC voltage in the transfer multipole of from about 2 to about 4 V, e.g. from about 3 to about 4 V; (xiv) a voltage in the C-trap entrance lens of from about 0 to about 7 V, e.g. from about 2 to about 4 V, e.g. from about 5 to about 6 V.

It will be appreciated that any of conditions (i) to (xi) may be applied alone or in combination with one or more, or all, of the other conditions.

Preferably, minimal activation energy is used to dissociate the protein from the detergent. In an embodiment, the laboratory frame energy is from about 500 to about 5000 electron volts, e.g. from about 500 to about 1500 electron volts. The term "laboratory frame energy" as used herein refers to the collision voltage multiplied by charge state of the protein.

It will be appreciated that the values described above represent the magnitude of the settings on the mass spectrometer. The values themselves may be positive or negative, depending on whether the mass spectrometer is operated in positive or negative mode. Typically, the mass spectrometer will be operated in positive polarity. A person of skill in the art will understand which values are negative and which values are positive in each mode.

The ionised protein is then resolved and detected and, if desired, further characterised. In particular, in embodiments in which the protein is in the form of a complex with a ligand, ions in which the ligand is bound to the protein or a fragment thereof can be detected directly using the mass spectrometer, rather than inferred indirectly from mass spectra of the separate components (ligand and protein). Moreover, where the solution or the complex comprises more than one ligand, the binding of one or more of said components to the protein may be detected simultaneously. For instance, the method may comprise detecting a plurality of ions selected from the group consisting of ions containing the therapeutic agent bound to the protein or a fragment thereof, ions containing one or more additional components (e.g. selected from lipid and nucleotides) bound to the protein or a fragment thereof, and ions in which the therapeutic agent and one or more additional components are bound to the protein or a fragment thereof. Thus, the present methods may be used to detect concomitant binding of the protein with e.g. a therapeutic agent and one or more other species which compete for binding sites. The binding of one or more dendritic detergent molecules to the protein, optionally concomitantly with one or more ligands, may also be directly detected.

In embodiments, the protein may be detected using ion mobility-mass spectrometry (IM-MS). In this case, the mass spectrometer may comprise an ion mobility cell to assess the folded state of protein complexes. The use of IM-MS may allow the stoichiometry of ligand agent binding, and the overall effects of ligand binding on the dynamics, stabilities, oligomeric structures and conformations of proteins, to be determined. For instance, the stoichiometry and oligomeric structure of complexes may be characterised by assessing mass differences. As a further example, dynamics, stabilities and conformations may be characterised by changes in charge states or by differences in arrival time distributions (i.e. ion mobility).

The protein may also be detected using tandem mass spectrometry (MS-MS).

Methods for the detection of membrane proteins, as well as complexes thereof, by mass spectrometry are disclosed in WO 2012/172378 and WO 2014/096821, the contents of which are incorporated herein by reference.

Extracting a Membrane Protein from its Native Membrane

The dendritic detergents described herein may also be used in a method of extracting a membrane protein from its native membrane.

This method involves providing a membrane protein in its native membrane. It is well-understood in the art that native membranes are those membranes in an organism in which the membrane protein is present.

The step of providing a membrane protein in its native environment may comprise expressing the membrane protein in an organism. In embodiments, the method may comprise overexpression a membrane protein in an organism, for instance by introducing gene vectors for overexpression of the membrane protein into the organism. Typically bacteria such as E. coli will be used. Mammalian cell lines (e.g. 293T), insect cells and yeast may also be used. Methods in which membrane proteins are overexpressed are known in the art and are described e.g. in Laganowsky et al., Nat. Protoc. 2013, 8, 639-651 (see also Drew et al., Nat. Protoc. 2008, 3, 784-798).

Following expression of the membrane proteins, the cells may be collected, e.g. by centrifugation. The cells may be then lysed, e.g. using a lysis buffer, to provide a lysate. Suitable lysis buffers may comprise tris(hydroxymethyl)aminomethane ('Tris', e.g. about 20 mM). Other components in the lysis buffer may include NaCl (e.g. about 300 mM). The pH of the lysis buffer may be from about 7 to about 8, e.g. 7.4. In preferred embodiments, then lysate will be homogenised, e.g. by being passed through a microfluidizer, and insoluble material removed by centrifugation.

The lysed membranes may be suspended in a buffer. Suitable buffers include Tris (e.g. about 20 mM). Other components in the buffer may include NaCl (e.g. about 100 mM) and/or glycerol (e.g. 0.2 v/v). The suspension may be homogenised, e.g. using a pestle and glass tube.

One the protein has been provided in its native membrane, it is contacted with a dendritic detergent as described herein. The dendritic detergent extracts the membrane protein from its native membrane and forms a detergent aggregate in which the membrane protein is contained. The dendritic detergents of the present invention may extract high levels of membrane protein, whilst advantageously maintaining the membrane protein in an intact, folded state.

The dendritic detergent may be contacted with the membrane protein in a molar ratio of dendritic detergent to membrane protein of from 10:1 to 150:1, e.g. from about 30:1 to about 125:1, e.g. from about 50:1 to about 100:1. In a preferred embodiment, the molar ratio of the detergent to the membrane protein is less than or equal to 100:1.

The dendritic detergent is preferably contacted with the membrane protein to give an aqueous solution containing the detergent at a concentration at least equal to, and preferably at two times the critical aggregation concentration (CAC) of the detergent.

In an embodiment, the dendritic detergent is present in the aqueous solution at a concentration of from about 100 µM to about 100 mM, e.g. from about 100 µM to about 200 µM. In an embodiment, the protein is present in the solution at a concentration of from about 1 nM to about 1 mM, e.g. from about 800 nM to about 900 nM.

The protein in its native membrane may be contacted with the dendritic detergent for a period of greater than 4 hours, preferably greater than 12 hours, such as for 24 hours. The membrane protein and detergent mixture may be gently agitated during this period. The protein and dendritic detergent may be contacted under cooling conditions, e.g. at a temperature of lower than 15° C., preferably lower than 10° C., such as at 4° C.

The mixture of protein and dendritic detergent may be centrifuged to remove any larger pellets.

In some embodiments, the method of extracting a membrane protein from its native membrane may further comprise purifying the extracted membrane protein. For instance, the membrane protein may be purified using chromatography methods. Chromatography methods are believed to separate different membrane proteins that may be present in a cell membrane, as well as other components such as lipids. The membrane protein preferably remains contained within the dendritic detergent aggregate during chromatography.

Immobilized-metal affinity chromatography (IMAC) is particularly suitable for purifying membrane proteins, though gel-filtration chromatography (also known as size-exclusion chromatography) and amylose affinity chromatography may also be used. Further purification methods include dialysis.

EXAMPLES

The following non-limiting examples illustrate the present invention.
Methods
The following methods were employed in the experiments of the examples.
Determination of the Critical Aggregation Concentration of Dendritic Detergents Methods for determining CAC values are known in the art. CAC values for the dendritic detergents of the present invention were determined using the dynamic light scattering (DLS) procedure described in Skhiri et al., Soft Matter 2012, 8, 10618-10627. Specifically, serial dilutions with dendritic detergent concentrations between $10^{-8}$ and $10^{-2}$ M were prepared in MilliQ water. The individual samples were passed through a syringe filter (RC, 0.2 µm) and equilibrated for 16 hours at room temperature prior to their analysis. The samples were transferred into a quartz cuvette (material: Quarz Suprasil, width×length: 2 mm×10 mm) and analyzed with a Zetasizer Nano-ZS ZEN3600 (Malvem, UK). The instrument was operated with the Zetasizer Software (v7.11) and the following acquisition parameters were used:
   Material: Polystyrene Latex
   Dispersant: Water
   Sample viscosity parameters: Use dispersant viscosity as sample viscosity
   Temperature: 22.5° C.
   Equilibration time: 120 seconds
   Cell type: Quarz cuvettes
   Measurement angle: 173° Backscatter
   Measurement duration: Manual
   Number of runs: 11
   Run duration: 10 seconds
   Number of measurements: 3
   Delay between the measurements: 0 seconds
   Data processing: General purpose (normal resolution)

The derived count rate values obtained from three measurements (per concentration) were averaged and the logarithm of the derived count rate average was plotted against the logarithm of the concentration. The double logarithmic plots showed two characteristic regions: a) a flat region with low count rates at lower dendritic detergent concentrations and b) a linear growth in the derived count rate at higher dendritic detergent concentrations. The individual regions were fitted to linear functions and the CAC value was calculated from their intersection (x-value).
Measuring the Ratio of Regioisomers in Detergent Batches The molar ratio of the different regioisomers in detergent batches based on first generation triglycerol were determined by analytical reversed-phase (RP) high-pressure liquid chromatography (HPLC). Experiments were performed in isocratic mode with a system from Knauer, equipped with two Smartline 1000 pumps, variable wavelength UV detector 2500, and an Autosampler 3950. As stationary phase a pre-packed Kinetex EVO C18 column was used (pore size: 100 Å, particle size: 5 µm, length: 250 mm, diameter 4.6 mm), purchased from phenomenex. Degassed mixtures of $H_2O$ and MeOH were used (v.v) and thermally equilibrated upon mixing for at least 12 hours prior to use. Data processing and analysis was performed with ChromeGate Client Viewer (v.3.3.2) from Knauer.

The molar ratio of the different regioisomers in detergent batches based on second generation triglycerol [G2] was determined by $^{13}C$ NMR analysis (inverse-gated). The [G2] detergent batches were dissolved in deuterated methanol to final concentrations of about 200 to 300 mg/mL prior to analysis. The molar ratio of regioisomers was taken to be equal to the intensity ratio of the $^{13}C$ focal point signals.
Overexpression of E. coli Membrane Proteins The following steps were performed using a procedure of Laganowsky et al., Nat. Protoc. 2013, 8, 639-651. Gene vectors for overexpression of the His-tagged (6×His) membrane protein constructs AqpZ-GFP, AmtB-MBP and MATE-GFP were transformed into E. coli BL21 (DE3) Gold (Agilent). Several colonies were incubated in medium (LB Broth, 50 mL of 5 g/L yeast extract, 10 g/L peptone from casein, and 10 g/L sodium chloride) and grown overnight at 37° C. One liter of medium was subsequently incubated with overnight culture (7 mL) and grown at 37° C. until the culture reached an optical density value ($OD_{600\ nm}$) of 0.6-0.8. Next, isopropyl b-D-1-thiogalactopyranoside (IPTG) was added to the culture at a final concentration of 0.5 mM and the cultures were grown for another three hours at 37° C. The cells were subsequently collected by centrifugation (5.000×g, 10 min, 4° C.).

A similar procedure was used to prepare OmpF, specifically the procedure of Housden et al., Science 2013, 340 (6140), 1570-1574.

The membrane protein MBP-NTSR1-TrxA was prepared following the procedure in Yen et al., Nature 2018, 559, 423-427.

Extraction of Overexpressed E. coli Membrane Proteins

To prepare the E. coli membrane proteins overexpressed using the above method for extraction, the harvested cell pellets were resuspended in lysis buffer (20 mM Tris, 300 mM NaCl, pH=7.4) and supplemented with a protease inhibitor tablet (Roche). The cell suspension was homogenized by passing it several times through an M-110 PS microfluidizer (Microfluidics). Insoluble material was removed by centrifugation (20.000×g, 20 min, 4° C.) and the supernatant was again centrifuged (100.000×g, 2 h, 4° C.). The yielded membranes were resuspended in ice-cold resuspension buffer (20 mM Tris, 100 mM NaCl, 0.2 v/v glycerol) and homogenized using a Potter-Elvehjem Teflon pestle and a glass tube.

The membranes were subsequently solubilized with detergents of interest. To do so, membrane aliquots (0.5 mL) were treated with a mixture of resuspension buffer (3.5 mL) and an aqueous solution, which contained the detergent of choice (1 mL, 5 w %). The mixtures were agitated gently over night at a temperature of 4° C. and subsequently centrifuged (21.000×g, 40 min, 4° C.). The pellets were discarded and the supernatants were subjected to IMAC purification as described below.

Purification of E. coli Membrane Proteins

IMAC columns were packed by loading 500 µL Ni-Agarose suspension (Quiagen) into a 1000 µL empty column (Bio-spin chromatography columns, Bio-Rad). The suspensions were settled down by a short centrifugation step (1000×g, 1 min). The columns were opened on the bottom and washed with water (3×500 µL), IMAC wash buffer (1×500 µL, 50 mM Tris, 200 mM NaCl, 20 mM imidazole, 0.1 v/v glycerol, 2×CAC detergent of choice), IMAC elution buffer (1×500 µL, 50 mM Tris, 100 mM NaCl, 500 mM imidazole, 0.1 v/v glycerol, 2×CAC detergent of choice), and IMAC wash buffer (5×500 µL). The supernatant obtained upon centrifugation of the solubilized membranes was loaded on the IMAC columns and every column was washed with IMAC wash buffer (5×500 µL), and IMAC buffer mixture (2×500 µL of wash buffer/elution buffer mixture, v.v, 9:1). The wash solutions were discarded and the proteins were finally eluted using IMAC elution buffer (1×550 µL).

Detergent Exchange of E. coli Membrane Proteins

The purified solution of OmpF, originally extracted using octyl β-D-glucopyranoside, was detergent exchanged into different batches of detergent. Specifically, detergent exchange from OG to OGDs was performed by means of gel filtration chromatography. As stationary phase a pre-packed Superdex 200 10/300 GL column (GE Healthcare, product number 17-5175-01) was used, which was operated with an ÄKTA setup. Detergent-containing ammonium acetate buffer (200 mM) with OGD concentrations of about one or two times of its CAC were used as the mobile phase. The eluted protein samples were concentrated using Amicon-Ultra 0.5 mL centrifugal devices (MWCO=150 kDa) prior to their nESI-MS analysis using a modified Q Exactive nESI-MS instrument (Thermo-Scientific).

Buffer Exchange of E. coli Membrane Proteins into a nESI-MS Buffer

The freshly eluted protein solutions were concentrated in Amicon-Ultra 0.5 mL centrifugal devices (MWCO=150 kDa), diluted with IMAC wash buffer (500 µL) and concentrated again by centrifugation. Buffer exchange into nESI-MS buffer (ammonium acetate ~200 mM, 2×CAC detergent of choice or 1×CAC where detergent batch 1 used) was performed with a centrifugal buffer exchange device (Micro Bio-Spin 6. Bio-Rad).

UV/VIS Analysis of the Eluted E. coli Membrane Proteins

Buffer-exchanged E. coli membrane protein samples were concentrated to equal volumes and the relative protein concentrations were determined by UV/VIS spectroscopy using a NanoDrop photospectrometer (DeNovix). Every sample was analyzed by UV/VIS spectroscopy in triplicate. The obtained absorbance values ($A_{485}$ for AqpZ-GFP and $A_{280}$ for AmtB-MBP) were normalized to the values obtained from DDM and were plotted with standard deviation (±SD).

Mass Spectrometry for Membrane Proteins

Buffer-exchanged membrane protein solutions were vaporized by nESI and the proteins were transferred into a modified Q-Exactive mass spectrometer.

The Q-Exactive mass spectrometer was set up according to Gault et al., Nat. Methods 2016, 13, 333-336. Exemplary instrument parameters were: injection flatapole of 7.9 V, inter flatapole of 6.9 V, bent flatapole of 5.9 V and transfer multipole of 4 V, capillary voltage of 1.2 kV, source temperature of 25° C., voltage in the C-trap entrance lens 2V. The acceleration voltage applied in the higher-energy collisional dissociation (HCD) cell was optimized to 200 V to remove the detergent aggregates from the membrane protein ions. The pressure in HDC was maintained at $9 \times 10^{-10}$ mBar. Spectra were acquired with a noise level parameter of 3 applied and 10 microscans at 17500 resolution. Further data processing was performed with Excalibur and OriginPro v9.1.

Fluorescence Assay of Membrane Proteins

A fluorescence assay was carried out on neurotensin receptor 1 (NTSR1), a membrane protein, following previously reported methods (e.g. Sarkar et al., PNAS 2008, 105, 14808-14813; Yen et al., Sci. Adv. 2017, 3, 1-6). Specifically, NTSR1 was solubilized in detergents of choice. To all samples, a tenfold excess of a dye-labelled ligand, BODIPY-NT(8-13), was added. This ligand exhibits a high binding affinity exclusively to native NTSR1. Upon incubation for 60 minutes, the excess of ligand was removed by gel-filtration chromatography and the remaining fluorescence of the sample was measured with a fluorescence microplate reader. The detected fluorescence intensity was then divided by the protein concentration and the data were normalized to the intensity obtained from a reference detergent.

Preparation of Soluble Protein-Detergent Complexes (PDCs)

ß-Lactoglobulin (BLG) was dissolved in ammonium acetate (10 mM) buffer to a final concentration of 1 mg/mL. The protein samples (500 µL) were then loaded into Amicon-Ultra 0.5 mL centrifugal devices (Merck Millipore, Germany). The molecular weight cut-off (MWCOs) of the centrifugal devices was adjusted to the molecular weight of BLG (MWCO=10 kDa). The samples were concentrated (14.000×g, 10 min) using a Heraeus Pico 17 centrifuge (Thermo-Scientific, USA), diluted with ammonium acetate buffer (10 mM) to a final volume of 500 µL and concentrated again. This procedure was repeated five times. The protein concentration was determined upon the final centrifugation step by means of UV/VIS spectroscopy using the molar extinction coefficients at 280 nm of BLG ($17600 \text{ M}^{-1} \text{ cm}^{-1}$).

Equimolar protein detergent mixtures (1:1, 50 µM) were prepared by appropriate dilution to generate a 1:1 protein-detergent complex stoichiometry.

Nanoelectrospray Ionisation Mass Spectrometry of Soluble PDCs

The sample conditions, including protein concentration, buffer concentration and concentration of the amphiphilic molecule, were taken from Seo et al., Angew. Chem. Int. Ed. 2016, 55, 14173-14176. Mass spectra were measured in positive ion mode using a modified Ultima high-mass quadrupole-time of flight (Q-ToF) mass spectrometer (Waters Micromass, Manchester, UK) equipped with a Z-spray nanoflow ESI (nESI) ionization source. The required borosilicate capillaries were prepared according to Gath et al., Analyst. 2016, 141, 5502-5510. Data acquisition and analysis were performed by means of MassLynx (V4.1). Capillary voltage (1.2 kV), cone voltage (35 V), RF lens (50 V), collision gas pressure ($P_{argon}$~$5 \cdot 10^{-3}$ mBar) and collision voltage (2 V) were adjusted to optimize the intensity of singly bound protein-detergent complexes (PDCs) in the m/z range between 200 and 5000. External m/z calibration was performed by means of CsI solutions (20 mg/mL, $H_2O$: isopropanol, v:v, 1:1). The intensities obtained from the individual protein signals (apo form) were extracted from the mass spectra and plotted as a function of the protein charge state. The data were fitted to a Gaussian function and the charge state (x-value) at maximum intensity was takes as the average charge state ($z_{ave}$).

Tandem Mass Spectrometry (MS/MS) of Soluble PDCs and Determination of $CID_{50}$ For the tandem mass spectrometry experiments, the ions were selected according to their m/z using the quadrupole. The width of the isolated m/z channel was varied by using either high resolution (LM res: 3.3 V, HM res: 15 V) or low resolution settings (LM res: 3.3 V, HM res: 11.3 V). Ions of a specific m/z were subsequently activated by stepwise increasing the injection voltage into the collision cell (collision voltage of 2-30 V).

To determine the collision voltages required to dissociate 50% of the fully protonated PDC population during the dissociation experiments, $CID_{50}$ values were determined by plotting the disappearance of the precursor PDC ion population ($D_{PDC}$) against the collision voltage:

$$D_{PDC} = \frac{I_{PDC}}{I_{TIC}} - I_{off}$$

To do so, the intensity of the PDC ion population ($I_{PDC}$) was divided by the total ion count ($I_{TIC}$). In case of an overlap in m/z with other ion populations that did not dissociate under the applied collision voltages, a constant offset ($I_{off}$) was observed. This offset was subtracted from the individual $D_{PDC}$ values. The resulting data points were fitted to a sigmoid function, the curves were normalized and the collision voltage at 50% intensity was taken as the $CID_{50}$ value. Data analysis was performed manually by using Origin V9.1.

Preparation of Contaminated Soluble Protein Samples

Samples of BLG were purchased from Sigma-Aldrich (product number: L3908-250 MG). The samples were dissolved as purchased in ammonium acetate (100 mM) buffer to give a protein concentration of 20 µM.

Soluble protein-dendritic detergent mixtures were obtained by adding 0.08% by weight of the dendritic detergent to the dissolved sample.

Desalted samples were obtained by passing the membrane protein through a desalting column (column volume: 5 mL, product number GE17-1408-01). Desalting was performed according to the operation manual provided by the manufacturer.

Mass Spectrometry (MS) of Contaminated Soluble Proteins

For mass spectrometry experiments on contaminated soluble proteins, the samples were analysed on a Synapt G1 travelling wave instrument. Though this instrument is capable of carrying out ion-mobility mass spectrometry, the ion mobility set-up of the instrument was not applied. The instrument settings and conditions were similar to those used in other soluble protein MS experiments described herein.

Example 1: Preparation of Dendritic Detergents

Dendritic detergents of formula (1) were made from the building blocks shown in FIG. 1. The following table shows the molar ratio of the different regioisomers in various detergent batches based on first generation triglycerol [G1].

| Detergent | Head group-linker-tail | Molar Ratio $[G1]_a$:$[G1]_b$ |
| --- | --- | --- |
| 1 | [G1]-ether-C12 | 6:4 |
| 2 | [G1]-triazole-C12 | 6:4 |
| 2a | [G1]-triazole-C12 | 1:0 |
| 2b | [G1]-triazole-C12 | 0:1 |

The following table shows the ratio of the different regioisomers in various detergent batches based on second generation triglycerol [G2].

| Detergent | Head group-linker-tail | Molar ratio $[G2]_{aa}$:$[G2]_{ab}$:$[G2]_{bb}$ |
| --- | --- | --- |
| 3 | [G2]-ether-C18 | 4:4:1 |
| 4 | [G2]-carbamate-Chol | 9:5:1 |
| 5 | [G2]-triazole-DC12 | 9:5:1 |

The critical aggregation concentration (CAC) for the different detergent compositions was measured and is provided in the following table.

| Detergent | CAC (mM) |
| --- | --- |
| 1 | 0.70 |
| 2 | 0.55 |
| 2a | 0.47 |
| 2b | 0.39 |
| 3 | 0.30 |
| 4 | 0.16 |
| 5 | 0.06 |
| DDM | 0.11 |

Example 2: Membrane Protein Extraction Using Dendritic Detergents

Figure 2:
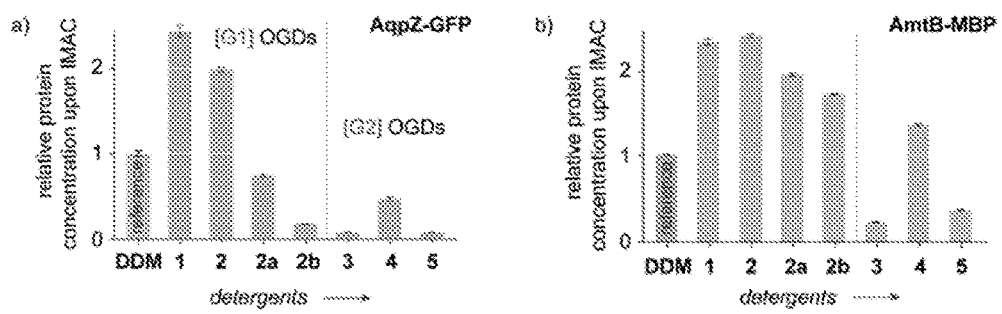
FIG. 2 shows the efficiency with which membrane proteins a) AqpZ-GFP and b) AmtB-MBP were extracted from biological membranes using different dendritic detergent batches and DDM as a reference detergent.

Three proteins were overexpressed in *E. coli* a) His-tagged aquaporin Z (AqpZ) fused to a green fluorescent protein (GFP); b) His-tagged ammonia channel (AmtB) fused to a maltose-binding protein (MBP); and c) multi-antimicrobial extrusion protein (MATE) fused to a GFP. Upon overexpression, the membranes of *E. coli* were isolated and extracted with dendritic detergent batches 1-5. DDM was also used as reference detergent. The so obtained protein solutions were purified by IMAC, buffer exchanged into a nESI-MS compatible buffer and the eluents concentrated to equal volumes. The protein concentration was monitored by UV/VIS spectroscopy and normalized to the values obtained for DDM. The level of AqpZ-GFP and AmtB-MBP in solution is shown in FIG. 2.

It can be seen that both AqpZ-GFP and AmtB-MBP are extracted by each of the dendritic detergent batches. High levels of extraction are obtained when first generation detergent batches are used, particularly those which contains a mixture of regioisomers.

Figure 3A:
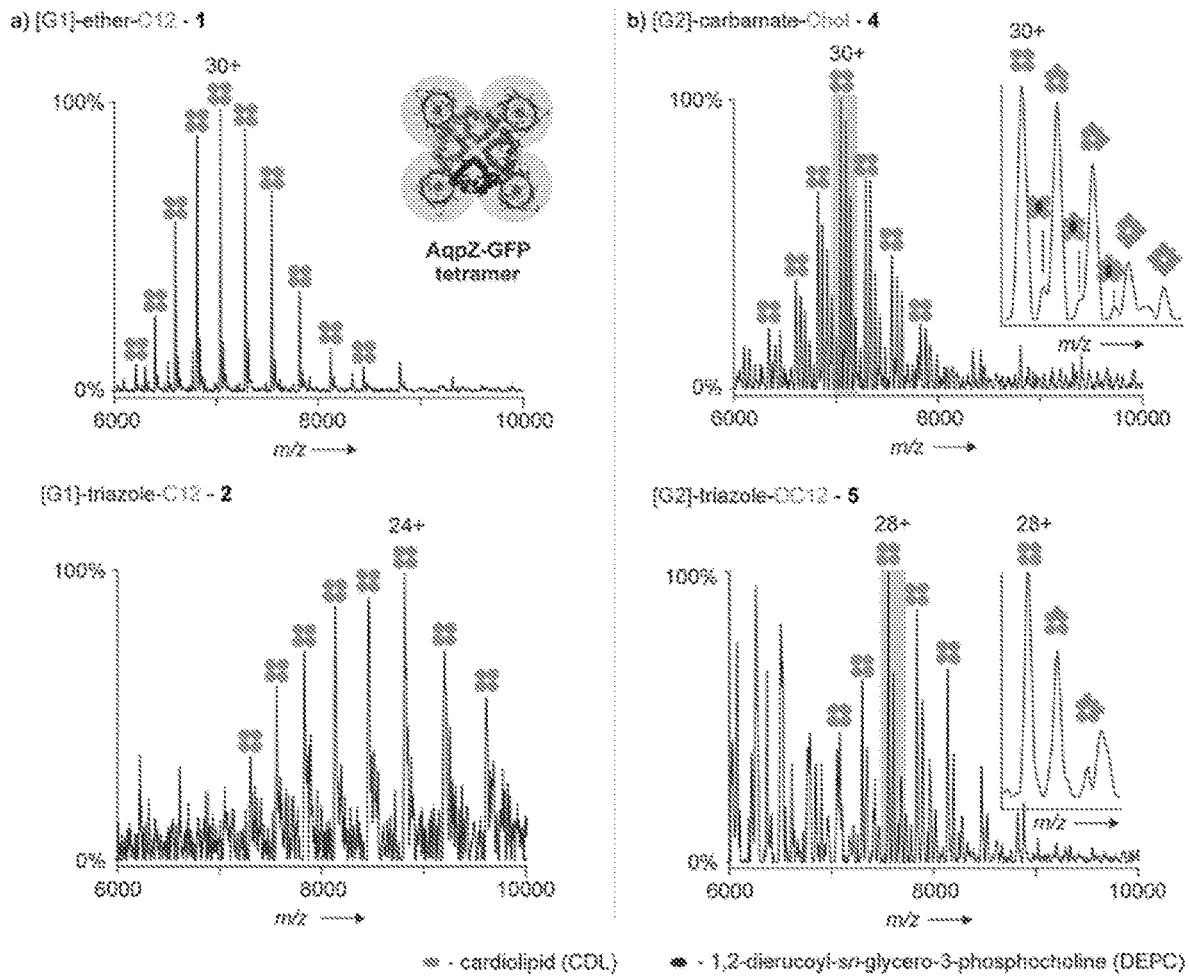
FIG. 3a depicts nESI mass spectra of the membrane protein AqpZ-GFP. Specifically, the figure shows: a) a mass spectrum of non-charge reduced tetrameric AqpZ-GFP (apo form) upon removal of [G1]-ether-C12; b) a mass spectrum of charge reduced tetrameric AqpZ-GFP (apo form) upon removal of [G1]-triazole-C12; c) a mass spectrum of non-charge reduced tetrameric AqpZ-GFP (apo form+CDL and DEPC bound states) upon removal of [G2]-carbamate-Chol; and d) a mass spectrum of charge reduced tetrameric AqpZ-GFP (apo form+CDL bound states) upon removal of [G2]-triazole-DC12.
Figure 3B:
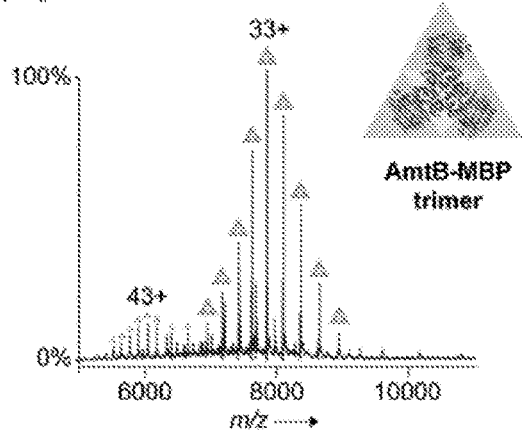
FIG. 3b depicts nESI mass spectra of the membrane protein AmtB-MBP. Specifically, the figure shows: a) a mass spectrum of non-charge reduced trimeric AmtB-MBP (apo form) upon removal of [G1]-ether-C12; b) a mass spectrum of charge reduced trimeric AmtB-MBP (apo form) upon removal of [G1]-triazole-C12; c) a mass spectrum of non-charge reduced trimeric AmtB-MBP (apo form+CDL and PI bound states) upon removal of [G2]-carbamate-Chol; and d) a mass spectrum of charge reduced trimeric AmtB-MBP (apo form+CDL bound states) upon removal of [G2]-triazole-DC12.
Figure 3B:
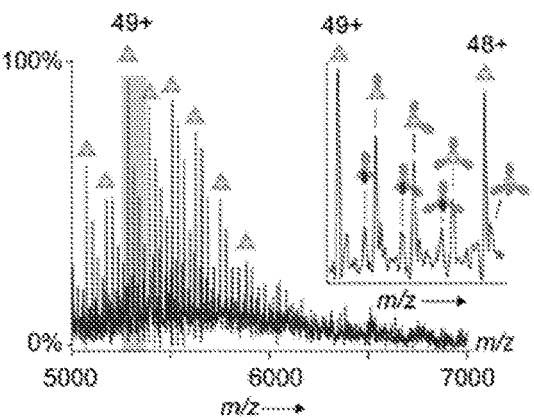
Figure 3B:
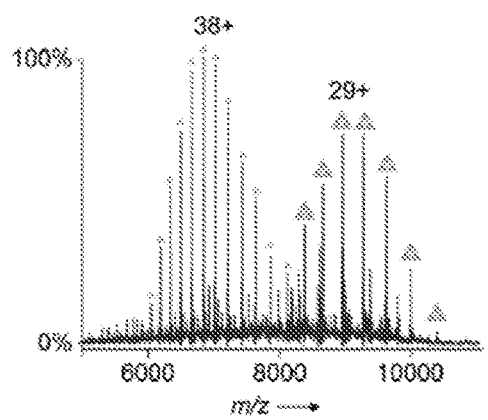
Figure 3B:
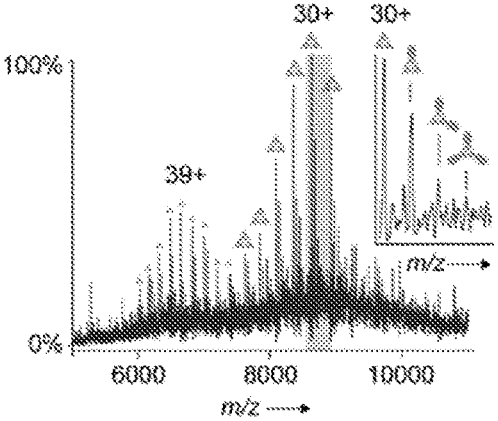
Figure 3C:
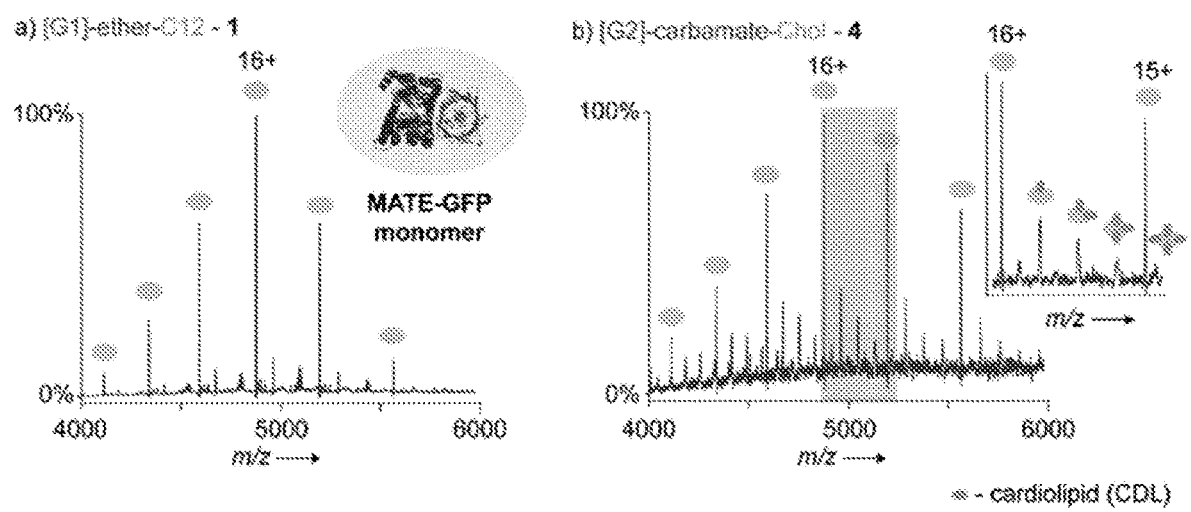
FIG. 3c depicts nESI mass spectra of the membrane protein MATE-GFP. Specifically, the figure shows: a) a mass spectrum of non-charge reduced monomeric MATE-GFP (mainly apo form) upon removal of [G1]-ether-C12; and b) a mass spectrum of non-charge reduced monomeric MATE-GFP (apo form+CDL bound states) upon removal of [G2]-carbamate-Chol.
Figure 4:
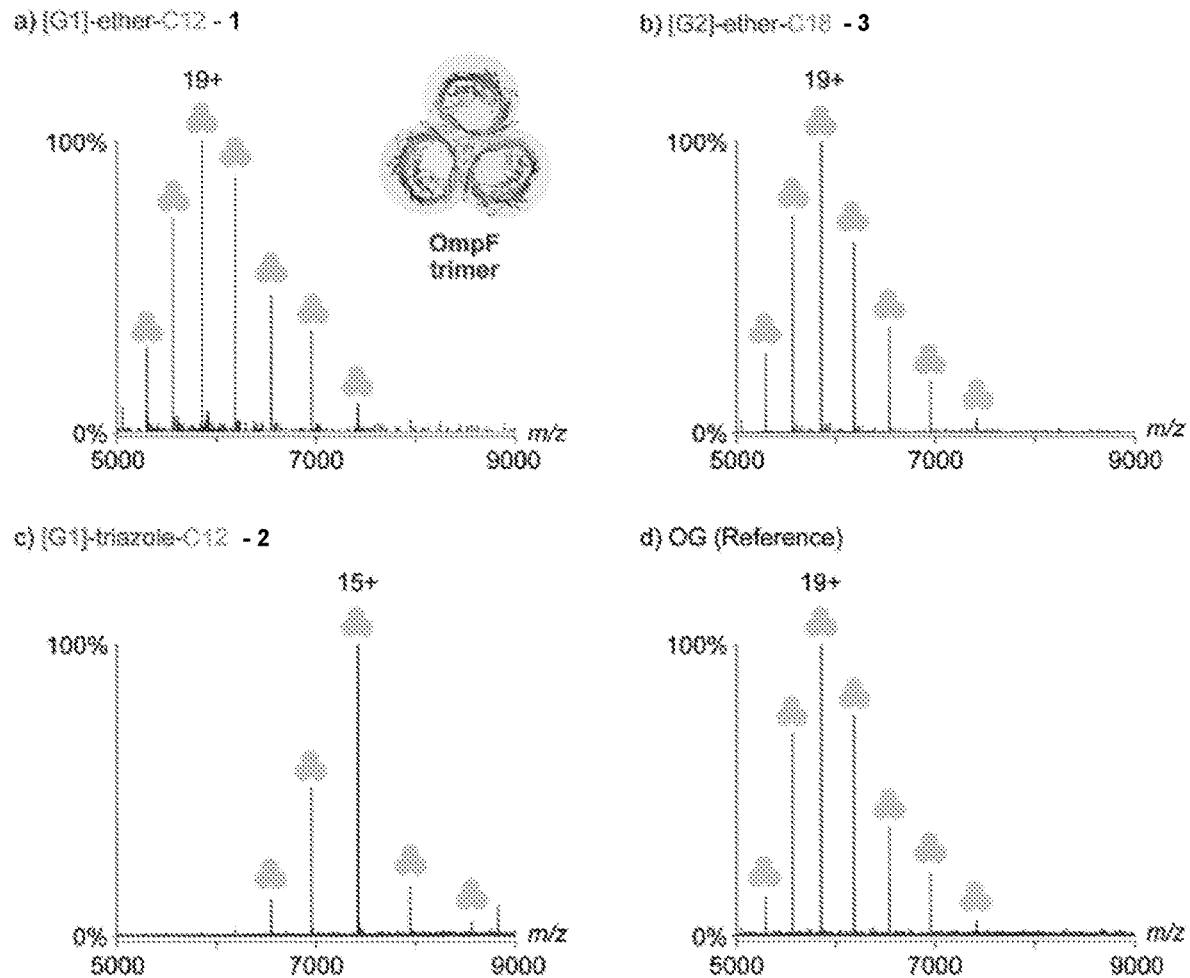
FIG. 4 shows nESI mass spectra of the trimeric membrane protein OmpF upon detergent exchange from detergent octyl β-D-glucopyranoside (OG) to different dendritic detergent batches, namely: a) [G1]-ether-C12, b) [G2]-ether-C18; and c) [G1]-triazole-C12. For comparison the mass spectrum taken from the reference OG is shown in d).

Example 3: nESI-MS Analysis of Membrane Proteins Extracted Using Dendritic Detergents The purified membrane protein solutions from Example 2 were vaporized by nESI and the proteins were transferred into a modified Q extractive mass spectrometer. The mass spectra of AqpZ-GFP, AmtB-MBP and MATE-GFP released from different detergent environments are shown in FIGS. 3a, 3b and 3c, respectively. The following table summarises the data obtained for AqpZ-GFP, AmtB-MBP and MATE-GFP, including the average charge state ($z_{ave}$), the lipid mass calculated from the mass spectrometer, the nature of the assigned lipid, and the molecular mass of the assigned lipid and OGD detergent.

solutions were vaporized by nESI and the proteins were transferred into a modified Q extractive mass spectrometer. The mass spectra of OmpF released from detergent batches 1-3 are shown in FIG. 4.

It can be seen that, whilst increasing the size of the dendritic detergent head group and tail did not have an effect on protein charge state, the use of a more basic linking group led to a substantial charge reduction of OmpF. These results are consistent with the findings in Example 2.

Example 5: Functional Integrity of Membrane Proteins in the Presence of Dendritic Detergents To evaluate the utility of dendritic detergents to preserve functional states of neurotensin receptor 1 (NTSR1), NTSR1 was solubilized in the reference detergent lauryl maltose neopentyl glycol (LMNG). This detergent does not facilitate the native MS analysis of this protein; however, it is known to preserve functional states of NTSR1 properly. Two samples of NTSR1 were then subjected to detergent exchange from LMNG to detergent batches 1 and 4. An excess of dye-labelled ligand, which exhibits a high binding affinity exclusively to native NTSR1, was added to the each sample. After incubation, excess ligand was removed and the fluorescence of the sample measured. The detected fluorescence intensity was divided by the protein concen-

| Protein | OGD | $z_{ave}$ | (Calculated Lipid Mass ± SD) [Da] | Assigned Lipid | Lipid Mass [Da]* | Detergent Mass [Da] |
|---|---|---|---|---|---|---|
| AqpZ-GFP | 1 | 30+ | — | — | — | — |
| | 2 | 25+ | — | — | — | — |
| | 2a | — | — | — | — | — |
| | 2b | — | — | — | — | — |
| | 3 | 29+ | — | — | — | — |
| | 4 | 30+ | (901 ± 2); (1414 ± 3) | DEPC; CDL | 898.3, 1430.0 | 947.6 |
| | 5 | 28+ | (1372 ± 4) | CDL | 1430.0 | 1055.6 |
| | DDM | — | — | — | — | — |
| AmtB-MBP | 1 | 43+/32+ | — | — | — | — |
| | 2 | 38+/29+ | — | — | — | — |
| | 2a | 38+/27+ | — | — | — | — |
| | 2b | 38+27+ | — | — | — | — |
| | 3 | — | — | — | — | — |
| | 4 | 48+ | (983 ± 3); (1400 ±1) | Pl; CDL | 977.1; 1430.0 | 947.6 |
| | 5 | 40+/30+ | (1394 ± 1) | CDL | 1430.0 | 1055.6 |
| | DDM | — | — | — | — | — |
| MATE-GFP | 1 | 16+ | (1407 ± 1) | CDL | 1430.0 | 408.3 |
| | 4 | 16+ | (1407 ± 1) | CDL | 1430.0 | 947.6 |

*taken from Laganowsky et al, Nature 2014, 510, 172-175

It can be seen that dendritic detergents having amore basic linking group, such as a triazole, reduces the charge states of the membrane protein on detergent removal. Enhanced lipid binding was observed when the larger second generation head group and a lipid-like hydrophobic residue, such as cholesterol or a branched hydrophobic tail.

Figure 5A:
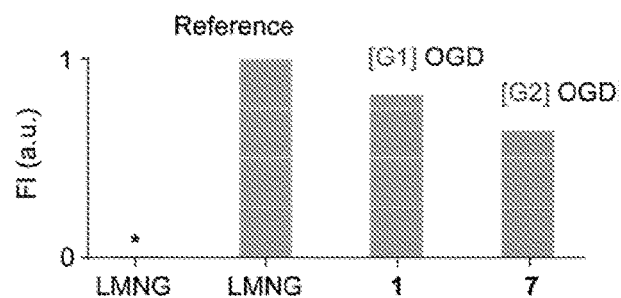
FIG. 5a shows the results of a normalized fluorescence intensity (FI) obtained from mixtures of the membrane protein NTSR1 and the fluorescent dye-labelled ligand BODIPY-NT(8-13) in different dendritic detergent environments.

Example 4: nESI-MS Analysis of Membrane Proteins Buffer Exchanged Using Dendritic Detergents The trimeric outer membrane protein (OmpF) was overexpressed in E. coli. Upon overexpression, the membranes of E. coli were isolated and extracted using octyl β-D-glucopyranoside as the detergent. The so obtained protein solution was purified by IMAC. The purified membrane protein solution was subjected to buffer exchange into a nESI-MS compatible buffer (200 mM ammonium acetate) supplemented with a dendritic detergent environments. The tration and the data normalized to the intensity obtained from the LMNG sample. As a control, NTSR1 solubilized in LMNG without the dye-labelled ligand was analysed, too. The results are shown in FIG. 5a.

It can be seen that, compared to LMNG, a slight reduction in fluorescence intensity is obtained for detergent batches 1 and 4. Accordingly, significant proportions of NTSR1 would appear to have retained functional upon detergent exchange from LMNG to dendritic detergent batches 1 and 4, particularly where a first generation detergent is used. The control sample showed no fluorescence intensity, confirming that any fluorescence intensity originates from the added dye-labelled ligand.

Figure 5B:
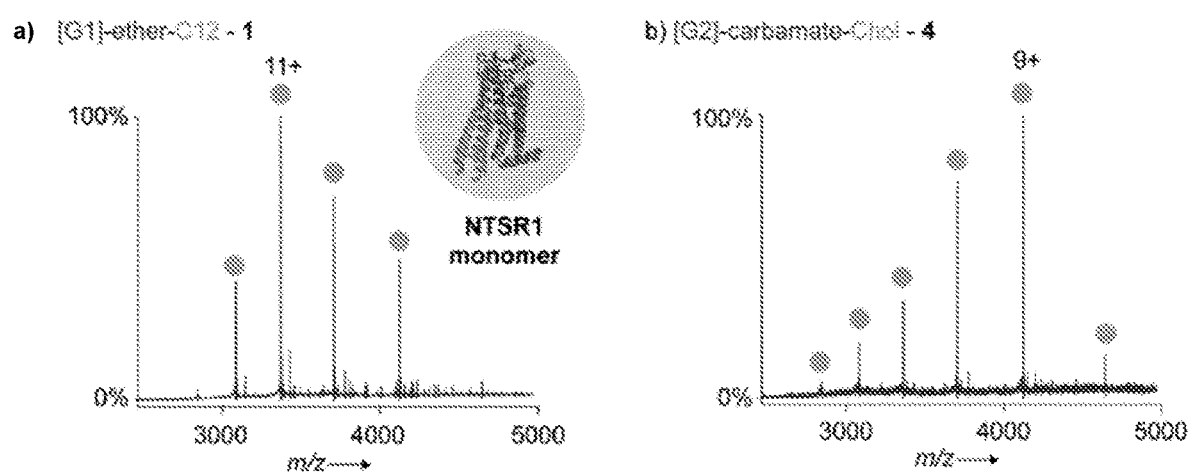
FIG. 5b shows nESI mass spectra of NTSR1 upon removal of the dendritic detergents a) [G1]-ether-C12; and b) [G2]-carbamate-Chol.

The detergent-exchanged samples of NTSR1 in detergent batches 1 and 4 were buffer exchanged into a nESI-MS compatible buffer supplemented with detergent batches 1 and 4. The solutions were vaporized by nESI and the proteins were transferred into a modified Q extractive mass spectrometer. The results are shown FIG. 5b.

It can be seen that detergent batches 1 and 4 facilitate mass spectrometry analysis of the membrane protein NTSR1, unlike the reference detergent LMNG.

Figure 6:
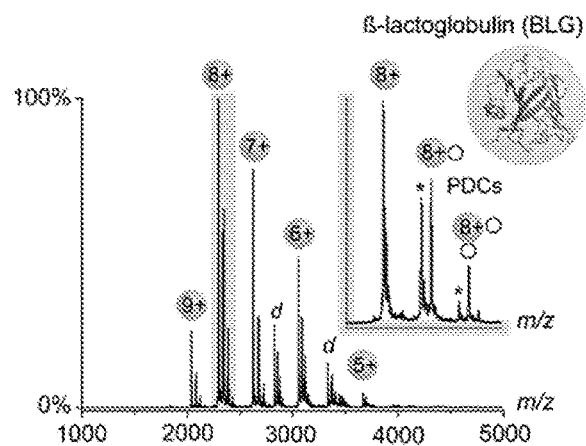
FIG. 6 depicts a mass spectrum of the soluble protein ß-lactoglobulin (BLG) in equimolar amounts with [G1]-ether-C12. BLG dimers are labelled with d, lactosylated forms of BLG are labelled with an asterisk, and detergent molecules are indicated with a circle. Complexes formed between BLG and [G1]-ether-C12 are generally denoted as protein-detergent complexes (PDCs).

Example 6: nEMS of Protein-Detergent-Complexes (PDCs) Using Dendritic Detergents A soluble protein ß-lactoglobulin (BLG) was transferred into the gas phase by nESI under conditions which optimized the intensity of protein-detergent-complex (PDCs) signals. The mass spectrum is shown in FIG. 6.

Three monomeric protein species that correspond to BLG bearing either no, one, or two covalently attached lactose moieties can be seen in the spectrum. For all monomeric forms of BLG the presence of PDCs was also detected.

Example 7: MS Charge Reduction of Soluble Proteins Using Alkali Metals

Figure 7:
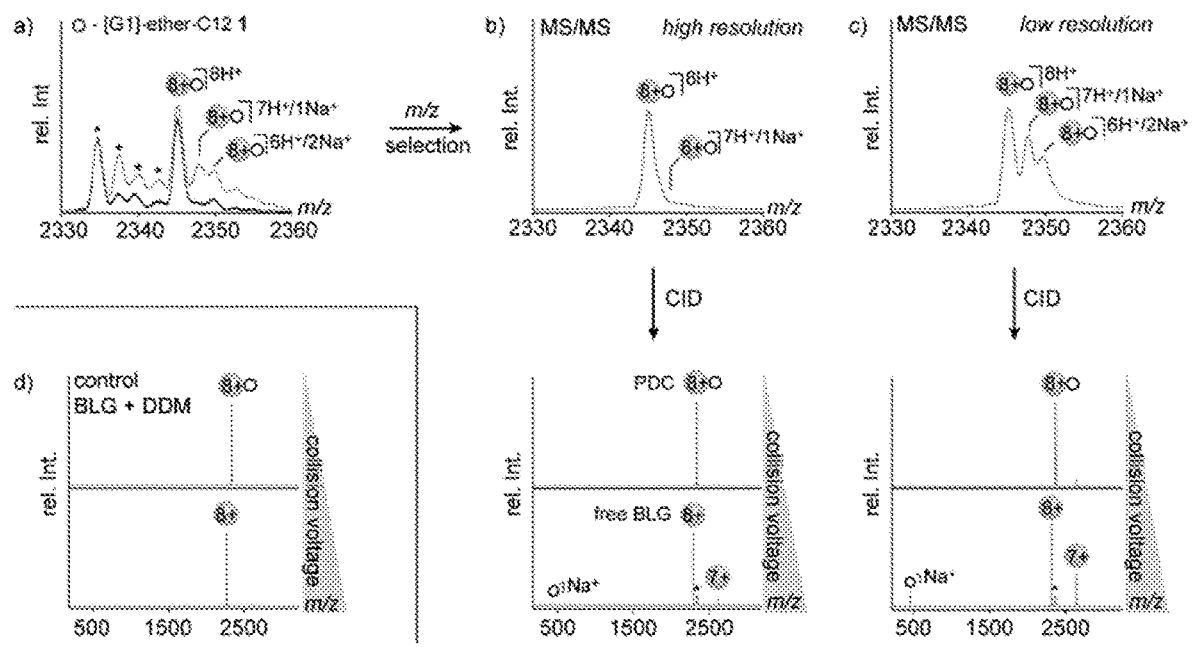
FIG. 7 depicts tandem mass spectra obtained before and after full dissociation of protonated and mixed protonated/sodiated PDCs (charge state 8+) formed by BLG and the dendritic detergent [G1]-ether-C12. Specifically the figure shows: a) mass spectra obtained before tandem mass spectrometry of sodiated (grey line) and non-sodiated (black line) PDCs; b) high resolution tandem mass spectra obtained before and after collision induced dissociation (CID); and c) low resolution mass spectra obtained before and after CID. For reference, a low resolution tandem mass spectrum obtained after CID where DDM has been used as the detergent is also included.
Figure 8:
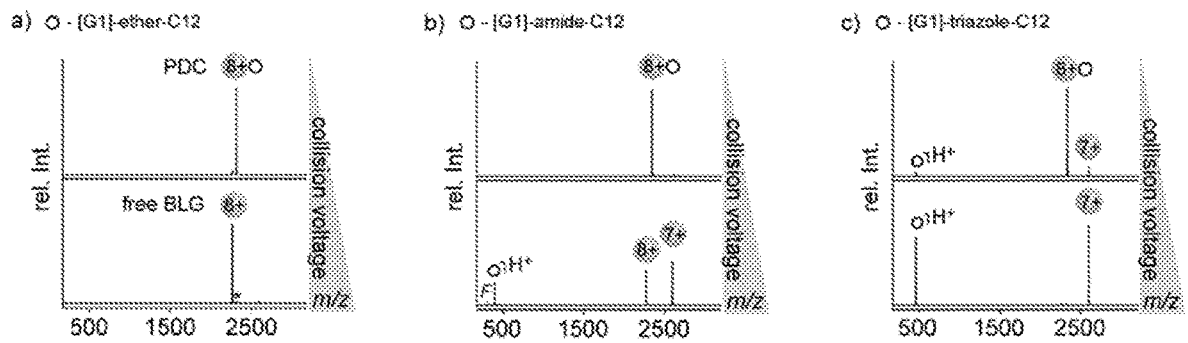
FIG. 8 depicts high resolution tandem mass spectra obtained after full dissociation of non-sodiated PDCs of BLG and different dendritic detergents, namely: a) [G1]-ether-C12; b) [G1]-amide-C12; and c) [G1]-triazole-C12.

To investigate the effect of alkali metal ions on the gas-phase dissociation of PDCs, sodium chloride (500 μM) was added to a sample of BLG PDCs. Tandem mass spectrometry focusing on the most abundant protein charge state 8+ was used to study dissociation behaviour of the sodiated BLG PDCs. The width of the isolated m/z channel 25 was varied by using either high resolution or low resolution settings. For reference, the same experiment was carried out in the presence of the detergent n dodecyl ß-D-maltoside (DDM) which is commonly used in native mass spectrometry. The results are shown in FIG. 7.

Where the non-basic dendritic detergent 1 was used, the appearance of three new ion populations was observed corresponding to BLG of two different charge states (8+ and 7+) and singly sodiated detergent ions (see FIGS. 7b and c). The extent of charge reduction upon complex dissociation was proportional to the relative amount of sodium within the PDC. This also suggests that dendritic detergent molecules that do not capture a sodium cation are dissociated from the complex as neutral species. Notably, no charge reduction of BLG is observed where DDM is used. Since DDM and the dendritic detergent in batch 1 exhibit similar alkyl spacers and linker groups, but differ in the structure of their head groups, the triglycerol head groups of the detergents in batch 1 are most likely the major coordination sites for sodium ions. These results show that alkali metals may be used to reduce the charge state of proteins during mass spectrometry experiments in which dendritic detergents are used.

Example 8: MS Charge Reduction in Soluble Proteins Using Dendritic Detergents To assess the impact of the linker group in the dendritic detergent on gas-phase dissociation of PDCs, tandem mass spectrometry experiments were conducted (without the addition of sodium chloride) using different detergent batches. The results are shown in FIG. 7.

High levels of charge reduction are observed in detergents containing an amide or triazole linker, with particularly high levels achieved where a triazole linker is used. This suggests that basic linker groups are able to pick up a proton from the PDC and dissociate as a cationic species. Minimal charge reduction of BLG is observed in the case of the detergent having an ether linkage, indicating that these detergent molecules dissociate as neutral species in the absence of sodium adducts. These results show that the linker group of a dendritic detergent may be used to adjust the charge state of proteins during mass spectrometry experiments.

Experiments were also conducted using dendritic detergents having a second generation ([G2]) head group, and similar trends were observed.

Example 9: Gas-Phase Stability of PDCs in the Presence of Dendritic Detergents The impact of the dendritic detergent structure on gas-phase stability of the PDC was assessed by determining the collision voltages required to dissociate 50% of the fully protonated PDC population during the CID experiment ($CID_5$). The results are shown in the following table, together with data summarising the extent of protein charge reduction observed in Example 8:

| OGD mixture | Charge reduction z-1 (%) | Stability $CID_{50}$ (V) |
| --- | --- | --- |
| [G1]-ether-C12 | 0 | 15 |
| [G1]-amide-C12 | 56 | 13 |
| [G1]-triazole-C12 | 100 | 11 |
| [G2]-ether-C18 | 0 | 30 |
| [G2]-amide-C18 | 43 | 25 |
| [G2]-triazole-C18 | 100 | 13 |

It can be seen that the detergents with the second generation head groups provide more stability to the gas-phase PDC than those with a first generation head group, perhaps due to the number of functional groups that likely contribute to protein-detergent interactions increasing by a factor of two, i.e. the ether backbone of oligoglycerol and the number of terminal hydroxyl groups. It would also appear that the extent of protein charge reduction is inversely correlated to the gas-phase stability of the PDC. These results show that the stability of a PDC can be controlled by altering the linker and/or head group in a dendritic detergent.

Example 10: Further Membrane Protein Extraction Using Dendritic Detergents

Figure 9:
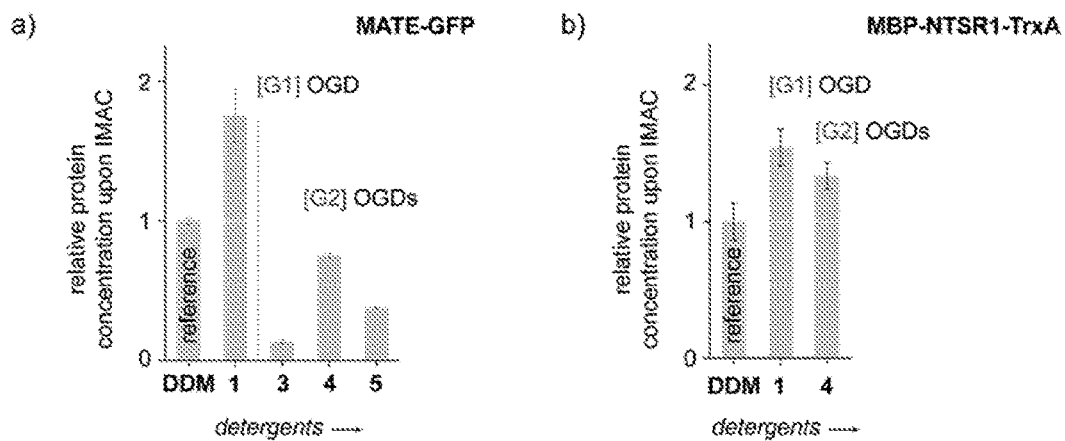
FIG. 9 shows the efficiency with which membrane proteins a) MATE-GFP and b) MBP-NTSR1-TrxA were extracted from biological membranes using different dendritic detergent batches and DDM as a reference detergent.

Experiments the same as those described in Example 2 were carried out on two further membrane proteins: a) MATE-GFP; and b) MBP-NTSR1-TrxA (TrxA denoting thioredoxin). The level of MATE-GFP and MBP-NTSR1-TrxA in solution is shown in FIG. 9.

It can be seen that both MATE-GFP and MBP-NTSR1-TrxA are extracted by each of the dendritic detergent batches. High levels of extraction are obtained when first generation detergent batches are used and, in the case of MBP-NTSR1-TrxA, also when second generation detergent batches are used.

Figure 10:
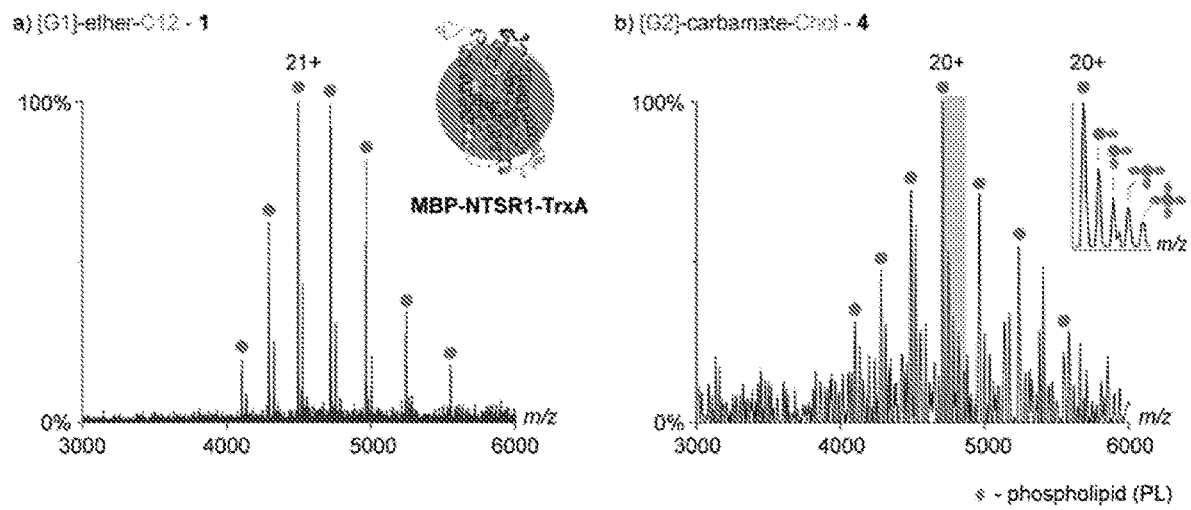
FIG. 10 depicts nESI mass spectra of the membrane protein MBP-NTSR1-TrxA. Specifically, the figure shows: a) a mass spectrum of non-charge reduced monomeric MBP-NTSR1-TrxA (mainly apo form) upon removal of [G1]-ether-C12; and b) a mass spectrum of non-charge reduced monomeric MBP-NTSR1-TrxA (apo form+PL bound states) upon removal of [G2]-carbamate-Chol.

Example 11: nESI-MS Analysis of a Further Membrane Protein Extracted Using Dendritic Detergents Experiments the same as those described in Example 3 were carried out on the membrane protein MBP-NTSR1-TrxA. The mass spectra of MBP-NTSR1-TrxA released from different detergent environments are shown in FIG. 10.

It can be seen that enhanced lipid binding was observed when the larger second generation head group and the lipid-like hydrophobic residue of cholesterol was used in the dendritic detergent.

Example 12: MS of Soluble Protein Samples Contaminated with Alkali Metals

Figure 11:
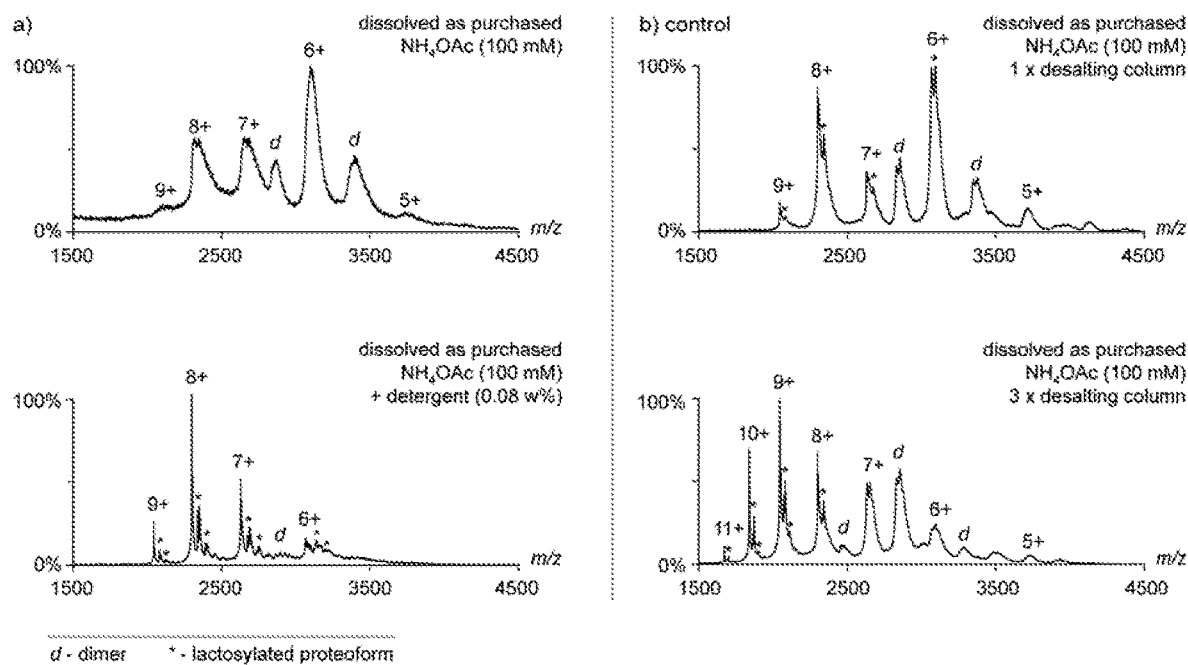
FIG. 11 shows mass spectra of the soluble protein BLG containing peak-broadening contaminants. Specifically, the figure shows: a) mass spectra of BLG dissolved in ammonium acetate buffer (top) and BLG dissolved in ammonium acetate buffer supplemented with [G1]-ether-C12 (bottom); and b) mass spectra of BLG from a sample that has been passed through a single desalting column (top), and a sample that has been passed through three desalting columns (bottom).

To investigate the effect of using dendritic detergents on soluble protein samples contaminated with an alkali metal salt, such as a sodium or potassium salt, mass spectrometry experiments were carried out in the presence and, for comparison, absence of a dendritic detergent ([G1]-ether-C12). For further comparison, samples purified using one or more desalting columns were also analysed. The results are shown in FIG. 11.

Characteristic peak broadening, which is known in the art to occur in mass spectrometry due to the presence of alkali metal contaminants, is observed with BLG in the absence of a dendritic detergent or further purification. The addition of a dendritic detergent allowed well-resolved signals of protonated BLG monomers, dimers, and even lactosylated proteoforms to be observed, thereby suggesting that the dendritic detergent depleted the number of salt adducts.

The use of a desalting column, and even multiple desalting column purification steps, did not give to mass spectra with a quality comparable to that obtained in the presence of a dendritic detergent.

The invention claimed is:

1. A method of detecting a protein by mass spectrometry, wherein the method comprises:
   (a) providing a solution comprising a dendritic detergent and a protein;
   (b) providing a mass spectrometer comprising a nanoelectrospray ionisation source, a mass analyser and a detector;
   (c) vaporising the solution using the nanoelectrospray ionisation source;
   (d) ionising the protein;
   (e) resolving the ionised protein using the mass analyser; and
   (f) detecting the resolved protein using the detector;
wherein the dendritic detergent is a non-ionic detergent comprising a dendritic head group linked to a hydrophobic tail, the dendritic head group comprising a branched alkyl group in which up to 1 in 2 carbon atoms may be replaced with an oxygen or nitrogen, provided that the dendritic head group further comprises at least 4 hydroxyl groups.

2. A method according to claim 1, wherein the protein is in the form of a complex with one or more ligands.

3. A method according to claim 1, wherein:
   the solution is an aqueous solution;
   the dendritic detergent is present in the solution at a concentration which is greater than or equal to the critical aggregation concentration of the dendritic detergent in said solution; and
   the molar ratio of the dendritic detergent to the protein in the solution is from about 0.5:1 to about 150:1.

4. A method according to claim 1, wherein the mass spectrometer is operated under one or more of the following conditions:
   (i) an injection flatapole voltage of about 2.0 to about 8.0 V;
   (ii) an inter flatapole lens voltage of about 2.0 to about 7.0 V;
   (iii) a bent flatapole voltage of about 2.0 to about 6.0 V;
   (iv) a transfer multipole of about 3.0 to about 5.0 V;
   (v) an acceleration voltage in the higher-energy collisional dissociation (HCD) cell of from about 0 to about 250 V;
   (vi) an in-source trapping activation of 0 to −300; and
   (vii) a pressure in the HCD cell of from about $8.0\times10^{-10}$ to about $2.0\times10^{-9}$ mBar.

5. A method according to claim 1, wherein the protein is detected intact.

6. A method according to claim 1, wherein the structure or conformation of the protein is characterised.

7. A method according to claim 1, wherein the protein is a membrane protein.

8. A method according to claim 1, wherein one or more hydrogen atoms on the protein have been exchanged for an alkali metal cation.

9. The method according to claim 1, wherein the solution comprising the dendritic detergent and protein is prepared by a method comprises:
   i. providing a protein in its native membrane;
   ii. contacting the protein with a dendritic detergent;
   iii. purifying the membrane protein;
wherein the detergent forms a detergent aggregate in which the membrane protein is contained.

10. A method according to claim 1, wherein:
    the branched alkyl group comprises from 1 to 20 branch points;
    the branched alkyl group contains from 1 in 6 to 1 in 2 carbon atoms replaced with an oxygen or nitrogen;
    the branched alkyl group is an acyclic alkyl group; and
    the dendritic head group comprises up to 50 hydroxy groups.

11. A method according to claim 1, wherein the linking group is selected from: hydrocarbylene, heterocyclylene, O, S, NR', NR'—O, C(O)NR', OC(O)NR', OC(O)O, O—$C_{1-4}$ alkylene-aryl, OC(=O)NR', NR'C(O)NR', NR'C(S)NR', C(NR')NR', C(O), S(O)$_2$, S(O), S(O)$_2$O, S—S, CR'=N, CR'=N—NR', C=N—NR'C(O), and combinations of up to three of these groups, where each R' is independently selected from H, $C_{1-4}$ alkyl and $C_{1-4}$ alkoxy.

12. A method according to claim 1, wherein the hydrophobic group comprises a $C_{6-100}$ alkyl group in which one or more methylene groups may be independently replaced by a unit selected from: $C_{2-6}$ alkenylene, $C_{2-6}$ alkynylene, arylene, O, S, NR'', NR''—O, C(O)NR'', OC(O)NR'', OC(O)O, NR''C(O)NR'', NR''C(S)NR'', C(NR'')NR'', C(O), S(O)$_2$, S(O), S(O)$_2$O, S—S, CR''=N, CR''=N—NR'', C=N—NR''C(O), where each R'' is independently selected from H, $C_{1-4}$ alkyl and $C_{1-4}$ alkoxy.

13. A method according to claim 1, wherein the dendritic detergent is in the form of a mixture of dendritic detergents having head groups which are regioisomers of one another.

14. A method according to claim 1, wherein the protein is in the form of a complex with one or more ligands selected from therapeutic agents, lipids, nucleotides and nucleosides.

15. A method according to claim 1, wherein one or more hydrogen atoms on the protein have been exchanged for a sodium cation.

16. A method according to claim 1, wherein the dendritic head group is an oligopolyol containing from 3 to 15 polyol monomers.

17. A method according to claim 1, wherein the dendritic detergent has the formula (I):

where: D represents the dendritic head group;
L represents a linking group; and
Hy represents the hydrophobic tail.

18. A method according to claim 17, wherein the linking group comprises an arylene group.

19. A method according to claim 1, wherein the dendritic head group is derived from a polyol.

20. A method according to claim 19, wherein the head group has the structure:

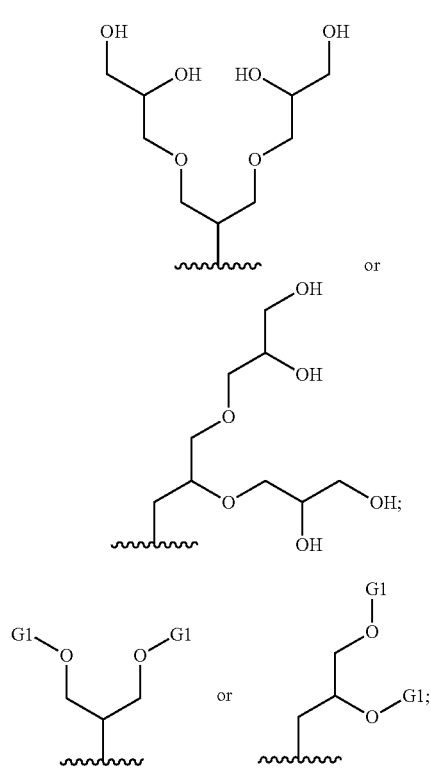
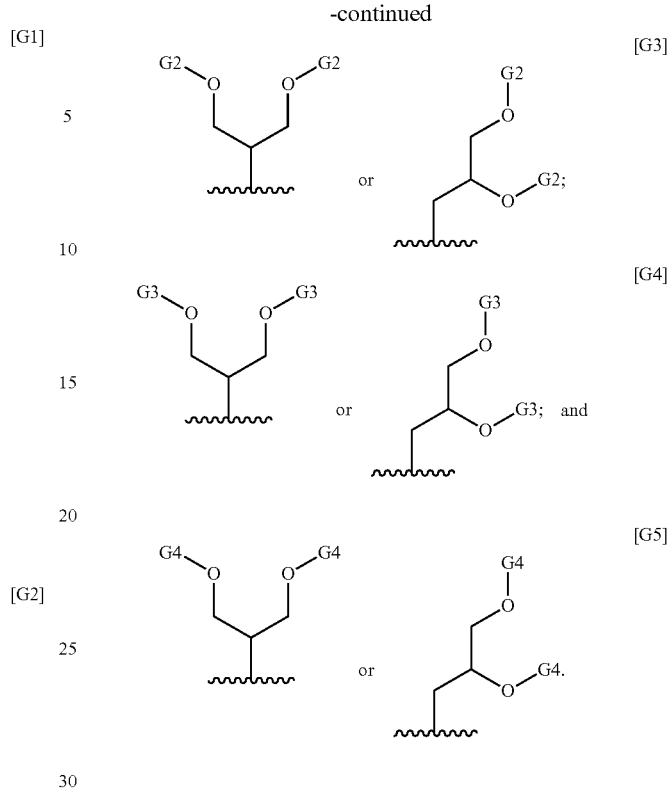
* * * * *

UNITED STATES PATENT AND TRADEMARK OFFICE
CERTIFICATE OF CORRECTION

PATENT NO. : 12,122,805 B2
APPLICATION NO. : 17/272614
DATED : October 22, 2024
INVENTOR(S) : Carol V. Robinson et al.

It is certified that error appears in the above-identified patent and that said Letters Patent is hereby corrected as shown below:

In the Claims

Column 31, Claim 3, Lines 43-46, replace "the dendritic detergent is present in the solution at a concentration which is greater than or equal to the critical aggregation concentration of the dendritic detergent in said solution; and" with -- the dendritic detergent is present in the solution at a concentration which is greater than or equal to a critical aggregation concentration of the dendritic detergent in said solution; and --.

Signed and Sealed this
Tenth Day of December, 2024

Katherine Kelly Vidal
*Director of the United States Patent and Trademark Office*